US011730454B2

(12) United States Patent
Song et al.

(10) Patent No.: US 11,730,454 B2
(45) Date of Patent: Aug. 22, 2023

(54) ULTRASOUND IMAGING APPARATUS AND METHOD OF CONTROLLING THE SAME

(71) Applicant: SAMSUNG MEDISON CO., LTD., Gangwon-do (KR)

(72) Inventors: Inseong Song, Daegu (KR); Yongmun Kang, Seoul (KR); Wongee Oh, Anyang-si (KR)

(73) Assignee: SAMSUNG MEDISON CO. LTD., Ganwon-Do (KR)

( * ) Notice: Subject to any disclaimer, the term of this patent is extended or adjusted under 35 U.S.C. 154(b) by 476 days.

(21) Appl. No.: 16/826,542

(22) Filed: Mar. 23, 2020

(65) Prior Publication Data

US 2020/0297324 A1    Sep. 24, 2020

(30) Foreign Application Priority Data

Mar. 22, 2019    (KR) ........................ 10-2019-0032772

(51) Int. Cl.
*A61B 8/00*    (2006.01)
*A61B 8/08*    (2006.01)

(52) U.S. Cl.
CPC .............. *A61B 8/54* (2013.01); *A61B 8/4263* (2013.01); *A61B 8/4461* (2013.01); *A61B 8/483* (2013.01); *A61B 8/58* (2013.01)

(58) Field of Classification Search
CPC ....... A61B 8/54; A61B 8/4477; A61B 8/4263; A61B 8/4461; A61B 8/483; A61B 8/58;
(Continued)

(56) References Cited

U.S. PATENT DOCUMENTS 4,892,103 A * 1/1990 Ogasawara ........... G01S 7/5206
73/620
6,551,245 B1 * 4/2003 Irioka ...................... A61B 8/12
600/463
(Continued)

FOREIGN PATENT DOCUMENTS

GB    2 216 660 A    10/1989
JP    2008-295958 A   12/2008
(Continued)

OTHER PUBLICATIONS

Extended European Search Report issued in corresponding European Patent Application No. 20163732.9 dated Aug. 18, 2020.

*Primary Examiner* — Patricia J Park
*Assistant Examiner* — Adil Partap S Virk
(74) *Attorney, Agent, or Firm* — Morgan, Lewis & Bockius LLP

(57)    ABSTRACT

Provided is an ultrasound imaging apparatus including: an ultrasound probe including a transducer module including an ultrasound transducer array, a driving device configured to rotate the transducer module, a magnet configured to rotate as a result of rotation of the transducer module, and a position sensor configured to output one of a first signal and a second signal on the basis of a change in magnetic flux density according to rotation of the magnet; and a controller configured to determine a first time for which the first signal is output as the transducer module rotates in a first direction, control the driving device to switch the rotating direction of the transduce module from the first direction to a second direction at a first switching time point at which an output signal is switched from the first signal to the second signal, control the driving device to switch the rotating direction of the transducer module one or more times during a time (Continued)

corresponding to the first time with respect to a second switching time point at which the output signal is switched from the second signal to the first signal after the first switching time point, determine a second time for which the first signal is output after the second switching time point, and determine a backlash value on the basis of a difference value between the first time and the second time.

17 Claims, 16 Drawing Sheets

(58) Field of Classification Search
CPC ..... A61B 8/4444; A61B 8/4488; A61B 8/461; A61B 8/488; A61B 8/5269; G01S 7/52046; G01S 15/8918; G01S 15/894

See application file for complete search history.

(56) References Cited

U.S. PATENT DOCUMENTS

| | | | |
|---|---|---|---|
| 2005/0288587 A1* | 12/2005 | Roh | A61B 8/00 600/445 |
| 2006/0241424 A1* | 10/2006 | Akiyama | A61B 8/4461 600/437 |
| 2007/0106155 A1* | 5/2007 | Goodnow | A61B 8/5276 600/437 |
| 2012/0065517 A1 | 3/2012 | Goodnow et al. | |
| 2013/0190726 A1* | 7/2013 | Kesner | A61M 25/0133 604/95.01 |
| 2016/0135785 A1* | 5/2016 | Song | A61B 8/4461 600/445 |

FOREIGN PATENT DOCUMENTS

| | | |
|---|---|---|
| KR | 10-2002-0038547 A | 5/2002 |
| KR | 10-1076917 B1 | 10/2011 |

* cited by examiner (A) IMAGE BEFORE
COMPENSATING
FOR BACKLASH VALUE (B) IMAGE AFTER
COMPENSATING
FOR BACKLASH VALUE

ULTRASOUND IMAGING APPARATUS AND METHOD OF CONTROLLING THE SAME

CROSS-REFERENCE TO RELATED APPLICATION

This application is based on and claims priority under 35 U.S.C. § 119 to Korean Patent Application No. 2019-0032772, filed on Mar. 22, 2019 in the Korean Intellectual Property Office, the disclosure of which is incorporated herein by reference.

BACKGROUND

1. Field

The disclosure relates to an ultrasound imaging apparatus for providing an ultrasound image by irradiating an ultrasound signal to an object and receiving an ultrasound echo signal reflected from the object, and a method of controlling the same.

2. Description of the Related Art

Recently, there has been a demand for an ultrasound imaging apparatus capable of realizing a three-dimensional (3D) image of an internal state of an object. In this regard, an ultrasound imaging apparatus capable of obtaining a 3D image by rotating a transducer module including an ultrasound transducer array has emerged.

However, the conventional ultrasound imaging apparatus does not compensate for a mechanical error occurring while the transducer module is rotating leftward or rightward to generate a 3D image, and when in use for many hours, the transducer module has a certain delay before switching the direction in response to a motor switching the direction, which is referred to as a backlash.

Accordingly, with an image obtained when the transducer module rotates in the clockwise direction and an image obtained when the transducer module rotates in the counterclockwise direction, an ultrasound image is caused to be shaken.

SUMMARY

Therefore, it is an object of the disclosure to provide an ultrasound imaging apparatus and a method of controlling the same, in which the position of a transducer module is measured on the basis of an output value of a position sensor, and the backlash value is compensated for, thereby providing a clear ultrasound image.

Additional aspects of the invention will be set forth in part in the description which follows and, in part, will be obvious from the description, or may be learned by practice of the invention.

Therefore, it is an aspect of the disclosure to provide an ultrasound imaging apparatus including: an ultrasound probe including a transducer module including an ultrasound transducer array, a driving device configured to rotate the transducer module, a magnet configured to rotate as a result of rotation of the transducer module, and a position sensor configured to output one of a first signal and a second signal on the basis of a change in magnetic flux density according to rotation of the magnet; and a controller configured to determine a first time for which the first signal is output as the transducer module rotates in a first direction, control the driving device to switch the rotating direction of the transducer module from the first direction to a second direction at a first switching time point at which an output signal is switched from the first signal to the second signal, control the driving device to switch the rotating direction of the transducer module one or more times during a time corresponding to the first time with respect to a second switching time point at which the output signal is switched from the second signal to the first signal after the first switching time point, determine a second time for which the first signal is output after the second switching time point, and determine a backlash value on the basis of a difference value between the first time and the second time.

The controller may determine the backlash value by dividing the difference value between the first time and the second time by a number of times the rotating direction of the transducer module is switched during the time corresponding to the first time with respect to the second switching time point.

The controller may control the driving device to rotate the transducer module in a same direction within a preset time from a point in time at which the rotating direction of the transducer module is switched, during the time corresponding to the first time with respect to the second switching time point.

The position sensor may switch the output signal from the second signal to the first signal when the magnetic flux density reaches a first magnetic flux density as the magnet moves toward the position sensor, and may switch the output signal from the first signal to the second signal when the magnetic flux density reaches a second magnetic flux density as the magnet moves away from the position sensor.

The controller may determine a third switching time point at which the output signal is switched from the second signal to the first signal as the magnet moves toward the position sensor as a result of the transducer module rotating in the first direction, and may determine a time difference between the third switching time point and the first switching time point to be the first time.

The controller may determine a fourth switching time point at which the output signal is switched from the first signal to the second as the magnet moves away from the position sensor as a result of the rotating of the transducer module after the time corresponding to the first time with respect to the second switching time point, and may determine a time difference between the second switching time point and the fourth switching time point as the second time.

The driving device may include a motor configured to generate a rotating power for rotating the transducer module.

The driving device may include a transmission device configured to transmit the rotary power of the motor to the transducer module.

The controller may control the motor to rotate at a preset speed.

The controller may further control the ultrasound probe to determine the backlash value when the ultrasound probe is connected to a main body of the ultrasound imaging apparatus.

The ultrasound imaging apparatus may further include an inputter configured to receive an input from a user, wherein the controller may control the ultrasound probe to determine the backlash value in response to receiving an input about photographing a three dimensional (3D) ultrasound image through rotation of the transducer module from the user, or receiving an input about determining the backlash value.

The controller may control the ultrasound probe at preset time intervals to determine the backlash value.

The ultrasound imaging apparatus may further include a display configured to display an ultrasound image, wherein the controller may control the display to output a notification or control the ultrasound probe to determine the backlash value again when the backlash value exceeds a preset threshold value.

The controller may, when controlling the driving device to switch the rotating direction of the transducer module, control the driving device to output a rotary power in a same direction during a time extended by a time corresponding to the backlash value to a preset time.

The controller may shift a rendering image corresponding to the first direction and a rendering image corresponding to the second direction from a central axis of the transduce module in directions corresponding thereto by an angle corresponding to the backlash value, to generate a rendering image of the ultrasound image.

The controller may determine a time difference between the first switching time point and the second switching time point as a third time, and may determine a time shortened by a time corresponding to the backlash value from the third time as an error time due to hysteresis characteristics of the position sensor.

When a point at which the output signal is switched from the second signal to the first signal as a result of the transducer module rotating in the first direction is set as a central axis of the transducer module, the controller may determine a point, which is shifted with respect to a point at which the output signal is switched from the first signal to the second signal as a result of the transducer rotating in the second direction by the error time in the first direction, as the central axis of the transducer module.

It is another aspect of the disclosure to provide a method of controlling an ultrasound imaging apparatus comprising an ultrasound probe including a transducer module including an ultrasound transducer array, a driving device configured to rotate the transducer module, a magnet configured to rotate as a result of rotation of the transducer module, and a position sensor configured to output one of a first signal and a second signal on the basis of a change in magnetic flux density according to rotation of the magnet, the method including: determining a first time for which the first signal is output as the transducer module rotates in a first direction; controlling the driving device to switch the rotating direction of the transduce module from the first direction to a second direction at a first switching time point at which an output signal is switched from the first signal to the second signal; controlling the driving device to switch the rotating direction of the transducer module one or more times during a time corresponding to the first time with respect to a second switching time point at which the output signal is switched from the second signal to the first signal after the first switching time point; determining a second time for which the first signal is output after the second switching time point; and determining a backlash value on the basis of a difference value between the first time and the second time.

The determining of the backlash may include determining the backlash value by dividing the difference value between the first time and the second time by a number of times the rotating direction of the transducer module is switched during the time corresponding to the first time with respect to the second switching time point.

The method may further include controlling the driving device to rotate the transducer module in a same direction within a preset time from a point in time at which the rotating direction of the transducer module is switched, during the time corresponding to the first time with respect to the second switching time point.

The position sensor may switch the output signal from the second signal to the first signal when the magnetic flux density reaches a first magnetic flux density as the magnet moves toward the position sensor, and may switch the output signal from the first signal to the second signal when the magnetic flux density reaches a second magnetic flux density as the magnet moves away from the position sensor.

The determining of the first time may include: determining a third switching time point at which the output signal is switched from the second signal to the first signal as the magnet moves toward the position sensor as a result of the transducer module rotating in the first direction; and determining a time difference between the third switching time point and the first switching time point.

The determining of the second time may include determining a fourth switching time point at which the output signal is switched from the first signal to the second as the magnet moves away from the position sensor as a result of the rotating of the transducer module after the time corresponding to the first time with respect to the second switching time point, and determining a time difference between the second switching time point and the fourth switching time point as the second time.

The driving device may include a motor configured to generate a rotating power for rotating the transducer module.

The driving device may include a transmission device configured to transmit the rotary power of the motor to the transducer module.

The method may further include controlling the motor to rotate at a preset speed The determining of the backlash value may include controlling the ultrasound probe to determine the backlash value when the ultrasound probe is connected to a main body of the ultrasound imaging apparatus.

The ultrasound imaging apparatus may further include an inputter configured to receive an input from a user, wherein the determining of the backlash value may include controlling the ultrasound probe to determine the backlash value in response to receiving an input about photographing a three dimensional (3D) ultrasound image through rotation of the transducer module from the user, or receiving an input about determining the backlash value.

The determining of the backlash value may include controlling the ultrasound probe at preset time intervals to determine the backlash value.

The ultrasound imaging apparatus may further include: a display configured to display an ultrasound image, wherein the method may further include controlling the display to output a notification or controlling the ultrasound probe to determine the backlash value again when the backlash value exceeds a preset threshold value.

The method may further include, when controlling the driving device to switch the rotating direction of the transducer module, controlling the driving device to output a rotary power in a same direction during a time extended by a time corresponding to the backlash value to a preset time.

The method may further include shifting a rendering image corresponding to the first direction and a rendering image corresponding to the second direction from a central axis of the transduce module in directions corresponding thereto by an angle corresponding to the backlash value, to generate a rendering image of the ultrasound image.

The method may further include determining a time difference between the first switching time point and the second switching time point as a third time, and determining a time shortened by a time corresponding to the backlash value from the third time as an error time due to hysteresis characteristics of the position sensor.

The method may further include, when a point at which the output signal is switched from the second signal to the first signal as a result of the transducer module rotating in the first direction is set as a central axis of the transducer module, determining a point, which is shifted with respect to a point at which the output signal is switched from the first signal to the second signal as a result of the transducer rotating in the second direction, by the error time in the first direction as the central axis of the transducer module.

BRIEF DESCRIPTION OF THE DRAWINGS

These and/or other aspects of the invention will become apparent and more readily appreciated from the following description of the embodiments, taken in conjunction with the accompanying drawings of which.

DETAILED DESCRIPTION

Figure 1:
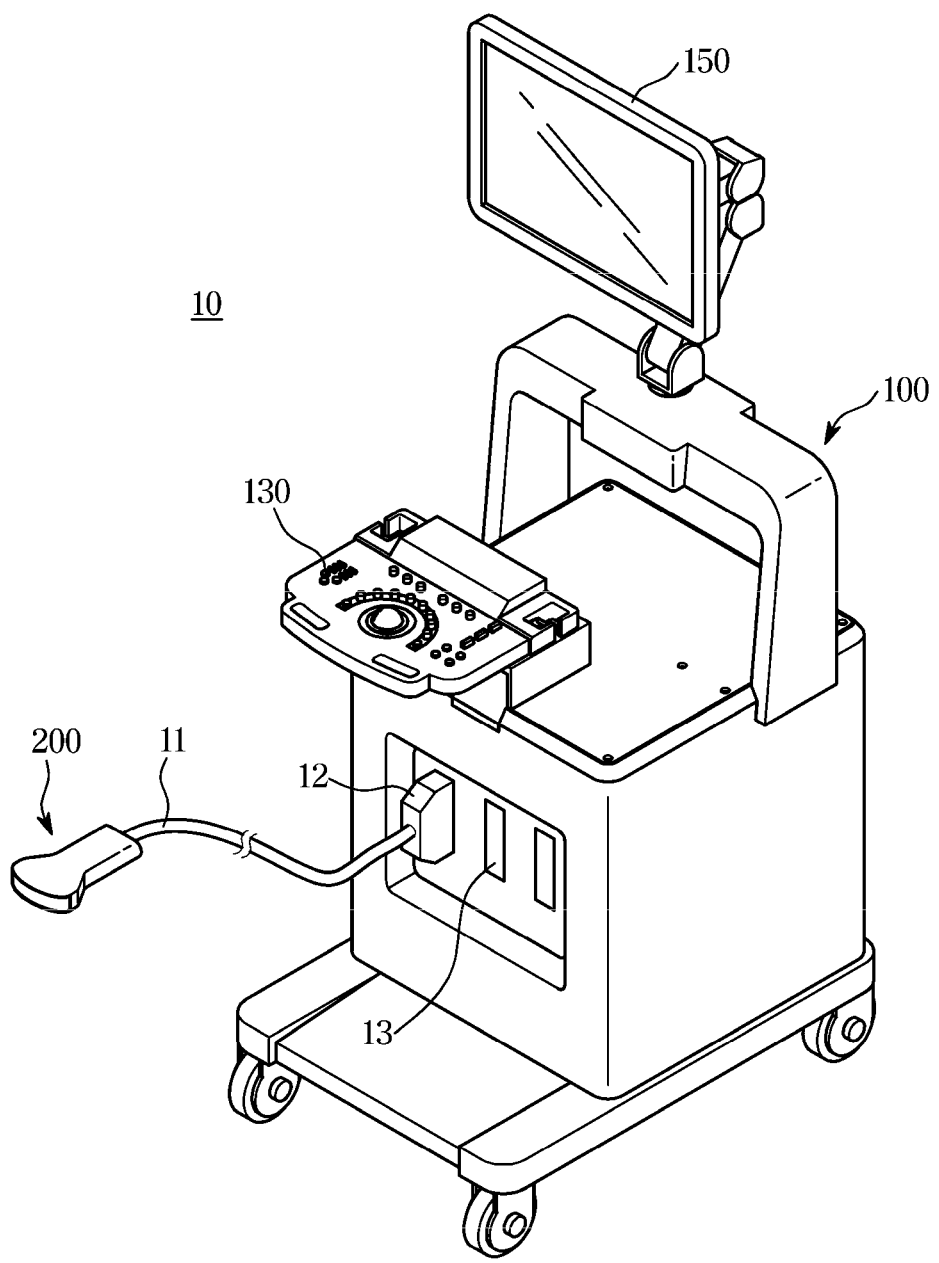
FIG. 1 is a diagram illustrating the external appearance of an ultrasound imaging apparatus according to an embodiment.

The embodiments set forth herein and illustrated in the configuration of the disclosure are only the most preferred embodiments and are not representative of the full the technical spirit of the disclosure, so it should be understood that they may be replaced with various equivalents and modifications at the time of the disclosure.

It will be further understood that the term "connect" or its derivatives refer both to direct and indirect connection, and the indirect connection includes a connection over a wireless communication network.

The terminology used herein is for the purpose of describing particular embodiments only and is not intended to limit the disclosure. It is to be understood that the singular forms "a," "an," and "the" include plural references unless the context clearly dictates otherwise. It will be further understood that the terms "include", "comprise" and/or "have" when used in this specification, specify the presence of stated features, integers, steps, operations, elements, and/or components, but do not preclude the presence or addition of one or more other features, integers, steps, operations, elements, components, and/or groups thereof.

The terms including ordinal numbers like "first" and "second" may be used to explain various components, but the components are not limited by the terms. The terms are only for the purpose of distinguishing a component from another. For example, a first element could be termed a second element, and, similarly, a second element could be termed a first element, without departing from the scope of the disclosure.

The terms including ordinal numbers like "first" and "second" may be used to explain various components, but the components are not limited by the terms. The terms are only for the purpose of distinguishing a component from another. Thus, a first element, component, region, layer or section discussed below could be termed a second element, component, region, layer or section without departing from the teachings of the disclosure.

Moreover, terms described in the specification such as "part," "module," and "unit," refer to a unit of processing at least one function or operation, and may be implemented by software, a hardware component such as a field-programmable gate array (FPGA) or an application-specific integrated circuit (ASIC), or a combination of software and hardware.

Reference numerals used for method steps are just used for convenience of explanation, but not to limit an order of the steps. Thus, unless the context clearly dictates otherwise, the written order may be practiced otherwise.

Hereinafter, embodiments according to the disclosure will be described in detail with reference to the accompanying drawings.

FIG. 1 is a diagram illustrating the external appearance of an ultrasound imaging apparatus according to an embodiment.

Referring to FIG. 1, the ultrasound imaging apparatus 10 according to the embodiment may include: an ultrasound probe 200 that transmits an ultrasound signal to an object, receives an ultrasound echo signal from the object, and converts the ultrasound signal into an electrical signal; and a main body 100 including an inputter 130 connected to the ultrasound probe 200 and receiving an input from a user and a display 150 configured to display an ultrasound image.

The ultrasound probe 200 according to the embodiment may be connected to the main body 100 through a cable 11 to receive various signals required for controlling the ultrasound probe 200, or transmit an analog signal or digital signal corresponding to the ultrasound echo received by the ultrasound probe 200 to the main body 100.

To this end, the cable 11 has one side end connected to the ultrasound probe 200, and the other side end with a connector 12 that may be coupled to or separated from a slot 13 of the main body 100. That is, the main body 100 and the ultrasound probe 200 may exchange control commands or data using the cable 11.

However, the embodiment of the ultrasound probe 200 is not limited thereto, and the ultrasound probe 200 may be implemented as a wireless probe to transmit and receive signals through a wireless network formed between the ultrasound probe 200 and the main body 100.

That is, when the ultrasound probe 200 is implemented as a wireless probe, the ultrasound probe 200 may be connected to the main body 100 through a wireless network instead of the cable 11, and the main body 100 and the ultrasound probe 200 may exchange control commands or data via a wireless network.

In addition, although one ultrasound probe 200 is connected to the main body 100 in FIG. 1, the disclosure is not limited thereto, and a plurality of the ultrasound probes 200 may be connected to one main body 100.

Meanwhile, a plurality of casters for mobility of the ultrasound imaging apparatus 10 may be provided at a lower side of the main body 100. The plurality of casters may allow the ultrasound imaging apparatus 10 to be fixed at a specific place or be moved in a specific direction. Such an ultrasound imaging apparatus 10 is referred to as a cart type ultrasound imaging apparatus.

However, unlike FIG. 1, the ultrasound imaging apparatus 10 according to the embodiment may be a portable ultrasound imaging apparatus that may be carried for a long distance movement. In this case, the portable ultrasound imaging apparatus may not include a caster. Examples of the portable ultrasound imaging apparatus may include a picture archiving and communication system (PACS) viewer, a smart phone, a laptop computer, a personal digital assistant (PDA), a tablet personal computer (PC), and the like, but are not limited thereto.

Hereinafter, components of the main body 100 and the ultrasound probe 200 of the ultrasound imaging apparatus 10 will be described in detail.

Figure 2:
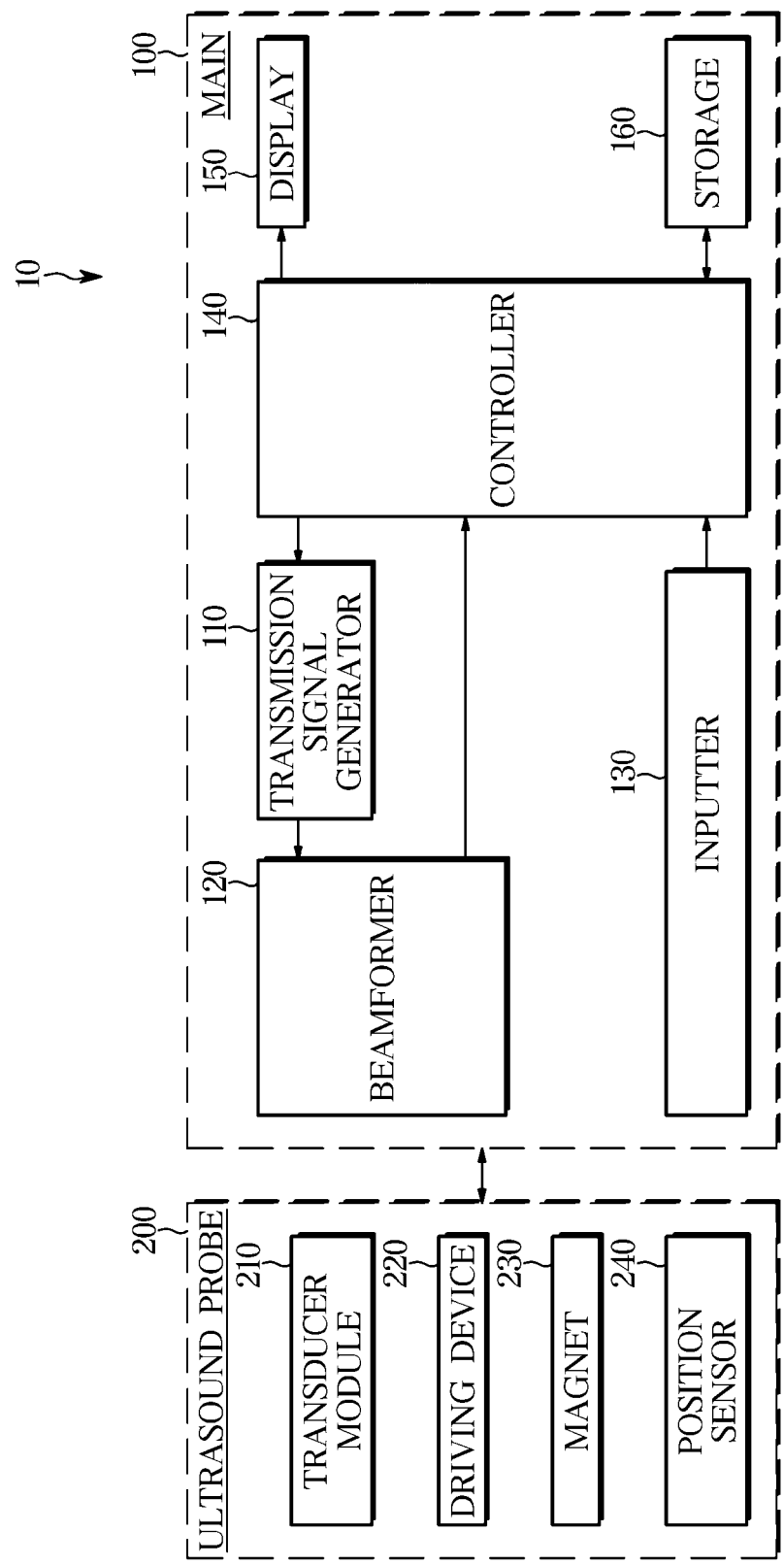
FIG. 2 is a control block diagram illustrating an ultrasound imaging apparatus according to an embodiment.
Figure 3:
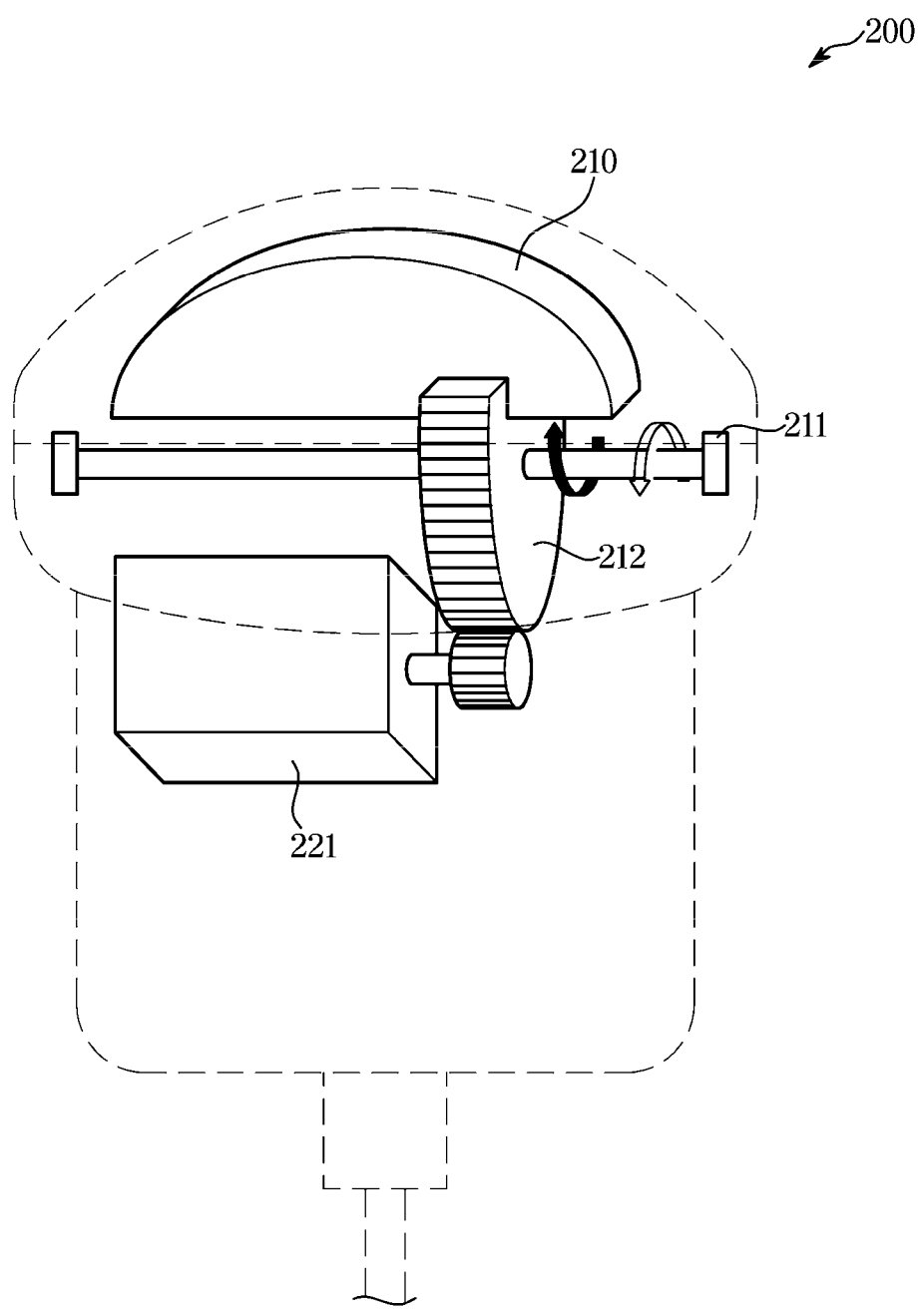
FIGS. 3 and 4 are perspective views illustrating an ultrasound probe according to an embodiment.
Figure 4:
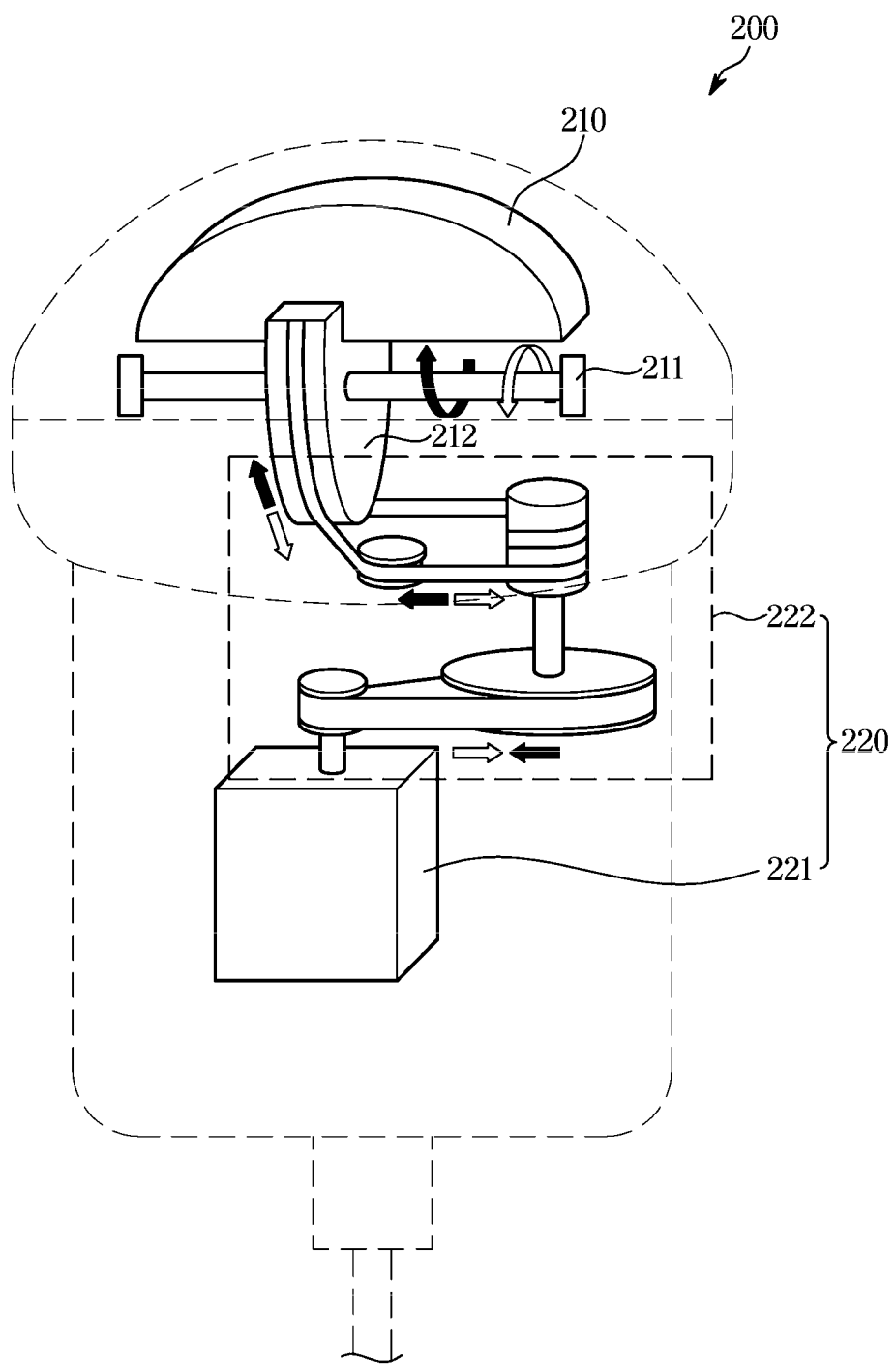
Figure 5:
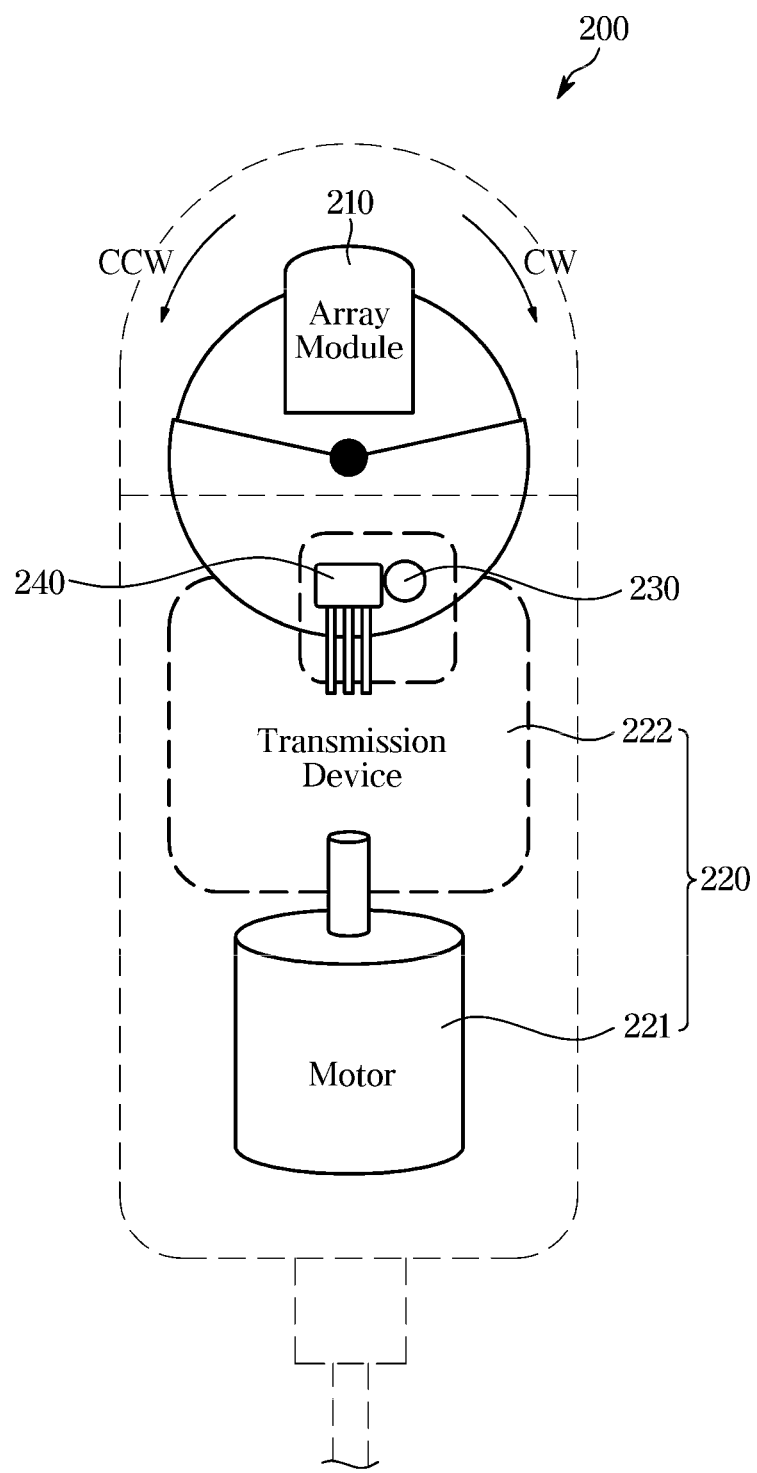
FIG. 5 is a schematic view illustrating an ultrasound probe according to an embodiment, when viewed from a side.

FIG. 2 is a control block diagram illustrating the ultrasound imaging apparatus 10 according to the embodiment, FIGS. 3 and 4 are perspective views illustrating the ultrasound probe 200 according to the embodiment, and FIG. 5 is a schematic view illustrating the ultrasound probe 200 according to the embodiment, when viewed from a side.

Referring to FIG. 2, the ultrasound probe 200 of the ultrasound imaging apparatus 10 according to the embodiment may include a transducer module 210 including an ultrasound transducer array, a driving device 220 for rotating the transducer module 210, a magnet 230 rotating according to rotation of the transducer module 210, and a position sensor 240 configured to output one of a high-level output signal and a low-level output signal on the basis of a change in magnetic flux density according to the rotation of the magnet 230.

The transducer module 210 according to the embodiment may include a plurality of transducer elements to perform conversion between an electrical signal and an ultrasound signal, transmit the ultrasound signal to an object, and receive an ultrasound echo signal reflected from the object.

Since the ultrasound waves are reflected in a varied degree according to the medium, the transducer module 210 may acquire information about the internal state of the object by collecting the ultrasound echo signals.

That is, the transducer module 210 may generate an ultrasound signal according to a pulse signal or an alternating current applied from a power source, and irradiate the ultrasound signal onto an object. The ultrasound signal irradiated onto the object is reflected from a targeted part inside the object as an ultrasound echo signal. The transducer module 210 receives the reflected ultrasound echo signal, and converts the received ultrasound echo signal into an electrical signal.

To this end, the transducer module 210 includes a piezoelectric layer in which a piezoelectric material vibrates to execute conversion between an electrical signal and an acoustic signal, a matching layer reducing an acoustic impedance difference between the piezoelectric layer and the human body so as to maximally transmit ultrasound waves generated from the piezoelectric layer to a target site of the human body, a lens concentrating ultrasound waves proceeding in the forward direction of the piezoelectric layer on a predetermined point, and a backing layer preventing ultrasound waves from proceeding in the backward direction of the piezoelectric layer to prevent image distortion.

In addition, the transducer module 210 is supplied with power current from an external power supply device or an internal power storage device, such as a battery. When supplied with power, piezoelectric vibrators or thin films forming the transducer module 210 vibrate. The transducer module 210 irradiates ultrasound waves generated due to the vibration of the piezoelectric vibrators or thin films to an object. Upon receiving ultrasound echo waves reflected from the object, the piezoelectric vibrators or thin films vibrate according to the received ultrasound echo signal. The transducer module 210 generates alternating current at a predetermined frequency corresponding to the vibration frequency of the piezoelectric vibrators or thin films, so that the ultrasound echo signal is converted into an electrical signal.

As such, the transducer module 210 includes a plurality of transducer elements for transmitting the ultrasound signal and receiving the ultrasound echo signal.

The transducer element may be provided, for example, using any one of a magnetostrictive ultrasonic transducer using a magnetostrictive effect of a magnetic body, a piezoelectric ultrasonic transducer using a piezoelectric effect of a piezoelectric material, or a capacitive micromachined ultrasonic transducer (cMUT), which transmits and receives ultrasonic waves using vibration of several hundreds or several thousands of micromachined thin films.

In addition, the transducer module 210 may receive ultrasound echo signals corresponding to a plurality of positions while rotating in a clockwise (CW) or counterclockwise (CWW) direction to acquire a three dimensional (3D) ultrasound image.

In this way, the ultrasound imaging apparatus 10 obtains two-dimensional (2D) cross-sectional images of the object in response to the received ultrasound echo signals, stacks the 2D cross-sectional images according to the positions thereof to generate a set of 3D arrays of discrete data, that is, volume data, and performs volume rendering on the volume data 3D to generate a 3D ultrasound image.

To this end, the ultrasound probe 200 may include the driving device 220 for transmitting a rotational force to the transducer module 210.

The driving device 220 according to the embodiment includes a motor for generating a rotational force to rotate the transducer module 210 clockwise or counterclockwise.

In this case, as shown in FIG. 3, the driving device 220 may be directly engaged with a rotating shaft 211 of the transducer module 210 to transmit the rotational force to the transducer module 210.

In detail, a gear of the motor 221 of the driving device 220 directly transmits a rotational force to a transmission member 212 of the rotating shaft 211, causing the rotating shaft 211 to be rotated, so that the rotational force is transmitted to the transducer module 210.

In addition, as shown in FIG. 4, the driving device 220 according to the embodiment may further include a transmission device 222 that transmits the rotational force generated by the motor 221 to the transducer module 210. In this case, the transmission device 222 may include, for example, at least one of a gear, a belt, a wire, or a linkage.

In this case, the gear of the motor 221 of the driving device 220 may transmit the rotational force to the transmission device 222, and the transmission device 222 may transmit the rotational force transmitted from the motor 221 to the transmission member 212 of the rotating shaft 211. Accordingly, the rotating shaft 211 is rotated, so that the rotational force is transmitted to the transducer module 210.

In this case, the transducer module 210 needs to rotate in accordance with the rotation of the driving device 220. Otherwise, a delay caused by a backlash occurs, and image shaking may occur due to the backlash between rotation of the driving device 220 and rotation of the transducer module 210. The backlash will be described below in detail.

The magnet 230 according to the embodiment may rotate according to rotation of the transducer module 210.

To this end, the magnet 230 may be attached to one surface of the transducer module 210, and as shown in FIG. 5, may be provided on the transmission member 212 that is rotated according to rotation of the transducer module 210.

However, the position of the magnet 230 is not limited to the above example, and the magnet 230 may be positioned without limitation as long as it can rotate in the same manner as the transducer module 210.

The position sensor 240 according to the embodiment may output one of a high-level output signal and a low-level output signal on the basis of a change in magnetic flux density according to the rotation of the magnet 230.

In detail, the position sensor 240 may switch the output signal from a high-level output signal to a low-level signal when the magnetic flux density reaches a first magnetic flux density as the magnet 230 moves toward the position sensor 240, and switch the output signal from a low-level output signal to a high-level output signal when the magnetic flux density reaches a second magnetic flux density as the magnet 230 moves away from the position sensor 240.

In this case, the first magnetic flux density at which the high-level output signal is switched to the low-level output signal and the second magnetic flux density at which the low-level output signal is switched to the high-level output signal are different from each other due to the hysteresis characteristic of the position sensor 240. The hysteresis characteristic of the position sensor 240 will be described below in detail.

According to the embodiment, the position sensor 240 may be a hall sensor using a hall effect, but the disclosure is not limited thereto, and the position sensor 240 may be implemented using various types of sensors as long as it can vary the output signal according to a change in magnetic flux density.

To detect a change in magnetic flux density according to the rotation of the magnet 230, the position sensor 240 may be positioned on a path in which the position sensor 240 is movable according to rotation of the magnet 230. In detail, as shown in FIG. 5, when the magnet 230 is provided on the transmission member 212, the position sensor 240 may be positioned at one side of the transmission member 212 to detect a change in magnetic flux density according to rotation of the magnet 230.

However, the position of the position sensor 240 is not limited to the above example, and the position sensor 240 may be variously located as long as it can measure a change in magnetic flux density according to rotation of the magnet 230.

With such a configuration, the ultrasound imaging apparatus 10 may determine rotation of the transducer module 210 and the positional change according to the rotation, on the basis of the output signal of the position sensor 240.

Referring again to FIG. 2, the main body 100 according to the embodiment may include a transmission signal generator 110 generating a transmission signal for generating an ultrasound signal irradiated onto an object, a beamformer 120 beamforming a received signal, an inputter 130 receiving an input from a user, a controller 140 determining a backlash value and generating an ultrasound image by compensating for the backlash value, a display 150 displaying an ultrasound image, and a storage 160 storing various types of information required for controlling the ultrasound imaging apparatus 10.

The transmission signal generator 110 according to the embodiment may generate a transmission signal according to a control command of the controller 140, and transmit the generated transmission signal to the ultrasound probe 200. Here, the transmission signal corresponds to a high voltage electrical signal for vibrating the plurality of transducer elements of the ultrasound probe 200.

The beamformer 120 according to the embodiment may perform conversion between an analog signal and a digital signal to convert a transmission signal (a digital signal) generated from the transmission signal generator 110 into an analog signal or convert an ultrasound echo signal (an analog signal) received from the ultrasound probe 200 into a digital signal, thereby supporting communication between the ultrasound probe 200 and the main body 100.

In addition, the beamformer 120 may add a time delay to the digital signal in consideration of the position of the vibrator and the focus point in order to overcome a difference in times taken for ultrasound waves to reach the focus point or a difference in times taken for ultrasound waves from the focus point to reach the vibrators.

That is, assuming that a plurality of transducer elements irradiate ultrasound signals, and a process of collecting all the ultrasound signals at a focus point is referred to as a focusing, the beamformer 120 may perform transmit focusing such that ultrasound signals generated from respective transducer elements are irradiated in a proper order suitable for overcoming the difference in times taken for the respective transducer elements to reach the focus point, and perform receive focusing such that ultrasound echo signals are arranged at the same time by assigning a proper time interval suitable for overcoming the difference in times taken for the ultrasound echo signals to reach the respective transducer elements.

The transmission signal generator 110 and the beamformer 120 may be included in the main body 100 as shown in FIG. 2, but may be provided in the ultrasound probe 200 and perform the function.

The inputter 130 according to the embodiment may receive an input relating to control of the ultrasound imaging apparatus 10 from a user.

In detail, the inputter 130 may receive, for example, a mode selection command regarding an amplitude (A) mode, a brightness (B) mode, a motion (M) mode, or a Doppler image.

In addition, the inputter 130 may receive an input for a 3D ultrasound image through rotation of the transducer module 210 from the user, and may receive an input for determination of a backlash value. In this case, the ultrasound imaging apparatus 10 may control the ultrasound probe 200 to determine the backlash value, which will be described below in detail.

In addition, the inputter 130 may receive a command to start ultrasound image photography from a user, or may receive a photographing protocol (e.g., a photographing part, a photographing time, etc.).

To this end, the inputter 130 may be provided in the main body 100 of the ultrasound imaging apparatus 10, for example, using a physical button, a knob, a touch pad, a touch screen, a stick type manipulation device, a trackball foot switch, a foot pedal, or the like. In this case, the inputter 130 provided as a touch pad or a touch screen may be provided on the display 150.

In addition, the inputter 130 may be provided as a separate input device, such as a keyboard or a mouse, connected to the ultrasound imaging apparatus 10 in a wired or wireless manner.

In addition, the foot switch or foot pedal may be provided at a lower side of the main body 100, and the user may control the operation of the ultrasound imaging apparatus 10 using the foot switch or the foot pedal.

The controller 140 according to the embodiment may generate an ultrasound image on the basis of the ultrasound echo signal received from the ultrasound probe 200.

In detail, the controller 140 may generate an ultrasound image through a scan conversion on the ultrasound echo signal.

Here, the ultrasound image may include not only a gray scale image obtained by scanning an object in A mode, B mode, and M mode, but also a Doppler image representing a moving object using a Doppler effect.

The Doppler image may include a blood flow Doppler image (a color Doppler image) representing a blood flow, a tissue Doppler image representing a tissue movement, and a spectral Doppler image displaying a moving speed of an object as a waveform.

For example, the controller 140 may extract a B mode component from the ultrasound echo signal received from the ultrasound probe 200 to generate a B mode image. Accordingly, the controller 140 may generate an ultrasound image in which the intensity of the ultrasound echo signal is represented in brightness on the basis of the B mode component.

Similarly, the controller 140 may extract a Doppler component from the ultrasound echo signal and generate a Doppler image in which the movement of the object is represented in color or waveform on the basis of the extracted Doppler component.

In addition, the controller 140 may generate a 3D ultrasound image by volume rendering a volume data acquired through the ultrasound echo signal.

In detail, the controller 140 may obtain 2D cross-sectional images of an object with respect to respective ultrasound echo signals at a plurality of positions obtained as a result of rotation of the transducer module 210, and stack the 2D cross-sectional images in a proper order of the positions thereof to generate a set of 3D arrays of discrete data, that is, a volume data, and perform volume-rendering on the volume data to generate a 3D ultrasound image.

In addition, the controller 140 may determine a delay time, i.e., a backlash value, generated on the basis of a backlash between the transducer module 210 and the driving device 220, before generating the ultrasound image.

In detail, the transducer module 210 needs to rotate in accordance with the rotation of the driving device 220. Otherwise, a delay caused by a backlash occurs.

The controller 140 may determine a delay time generated on the basis of the backlash, that is, a backlash value.

To this end, the controller 140 may control the driving device 220 to rotate the transducer module 210 in a preset pattern. In the preset pattern, the transducer module 210 may rotate in a first direction, and at a point where the magnet 230 passes through the position sensor 240, may switch the direction into a second direction.

Subsequently, in a case that the magnet 230 enters an area within a low-level output range of the position sensor 240, the transducer module 210 may perform the direction switching one or more times during a time corresponding to a first time taken for the magnet 230 to pass through the position sensor 240 as a result of the transduce module 210 rotating in the first direction. At this time, the magnet 230 is positioned within the low-level output range of the position sensor 240.

In this case, the low-level output range of the position sensor 240 may correspond to a range from a point when the magnetic flux density reaches a first magnetic flux density as the magnet 240 moves toward the position sensor to a point before the magnetic flux density reaches a second magnetic flux density as the magnet 230 moves away from the position sensor 240.

In addition, the first time is a period of time in which the magnet 230 moves toward the position sensor 230 and then moves away from the position sensor 240 while the transducer module 210 is moving in the first direction, that is, a time taken for the magnet 230 to pass through the low-level output range of the position sensor 240.

Then, the transducer module 210 may rotate until the magnetic flux density reaches the second magnetic flux density as the magnet 230 moves away from the position sensor 240, that is, until the magnet 230 deviates from the low-level output range of the position sensor 240

The controller 140 may determine a second time for which the magnet 230 has stayed within the low-level output range of the position sensor 240 after the transducer module 210 switches the rotating direction into the second direction, and determine a backlash value on the basis of a difference value between the first time taken for the magnet 230 to pass through the position sensor 240 during the first direction rotation of the transducer module and the second time.

In this case, the first direction may correspond to the clockwise direction (CW) or the counterclockwise direction (CCW), and the second direction may correspond to the reverse direction of the first direction. That is, when the first direction corresponds to the clockwise direction, the second direction corresponds to the counterclockwise direction, and when the first direction corresponds to the counterclockwise direction, the second direction corresponds to the clockwise direction.

Hereinafter, the first direction is described as the clockwise CW direction and the second direction is described as the counterclockwise CCW, but the disclosure is not limited thereto, thus it may also be understood that the first direction may be described as the counterclockwise CCW direction and the second direction may be described as the clockwise CW, direction.

The determining of the backlash value will be described below in detail.

In addition, after determining the backlash value, the controller 140 may compensate for the determined backlash value when the ultrasound image is taken.

When controlling the transducer module 210 to rotate while irradiating an ultrasound signal to acquire an ultrasound image, the controller 140 may compensate for the determined backlash value.

In detail, when controlling the driving device 220 to switch the rotating direction of the transducer module 210, the controller 140 may control the riving device 220 to output a rotational force in the same direction for a time extended by a time corresponding to the backlash value from a preset time.

In this case, the preset time may correspond to a time that is set for the transducer module 210 to rotate after switching the direction to provide a rotation angle determined according to a photographing protocol. By compensating for the rotation time of the transducer module 210 using the time extended by the time correspond to the backlash value from the preset time as described above, the transducer module 210 may be prevented from rotating an angle less than a desired rotation angle due to the backlash value.

In addition, the controller 140 may compensate for the backlash value by acquiring an ultrasound image of each of the clockwise and counterclockwise directions and correcting the ultrasound image corresponding to each of the clockwise and counterclockwise directions.

In detail, the controller 140 may shift each of a rending image corresponding to the first direction and a rendering image corresponding to the second direction in the direction corresponding thereto from the central axis of the transducer module 210 by an angle corresponding to the backlash value, so that a rendering image of the ultrasound image is generated. In this way, the ultrasound imaging apparatus 10 may provide an ultrasound image without shaking.

In addition, the controller 140 according to the embodiment may determine and compensate for an error time due to the hysteresis characteristic of the position sensor 240.

In detail, when controlling the transducer module 210 to rotate in a predetermined pattern, the controller 140 may determine a time from a point in time at which the magnet 230 passes through the position sensor 240 as a result of the transducer module 210 rotating in the first direction to a point in time at which the magnet 230 enters the low-level output range of the position sensor 240 as a result of the transducer module 210 switching the direction into the second direction as a third time, and may determine a difference value between the third time and the backlash value as an error time due to the hysteresis characteristic.

The controller 140 may control the transducer module 210 such that the transducer module 210 is positioned on the central axis of the rotation radius for the ultrasound image capturing. In this case, the controller 140 may set a point at which the output signal of the position sensor 240 is switched from the high-level output signal to the low-level output signal as a result of the transducer module 210 rotating in the first direction as the central axis of the transducer module 210, and store the set point in the storage 160.

In this case, when the controller 140 determines a point at which the output signal of the position sensor 240 is switched from the low-level output signal to the high-level output signal as a result of the transducer module 210 rotating in the second direction as the central axis of the transducer module 210, a difference occurs between the set central axis and the determined central axis due to the hysteresis characteristic of the position sensor 240.

Accordingly, the controller 140 may determine a point rotated from the point, at which the output signal of the position sensor 240 is switched from the low-level output signal to the high-level output signal as a result of the transducer module 210 rotating in the second direction, by the error time in the first direction as the central axis of the transducer module 210.

The controller 140 may include at least one memory for storing a program for performing the above-described operation and operations to be described below, and at least one processor for executing the stored program.

The display 150 according to the embodiment may display an ultrasound image generated from the controller 140, and according to embodiments, may display a notification indicating that the backlash value exceeds a preset threshold.

To this end, the display 150 may be provided in the main body 100 of the ultrasound imaging apparatus 10, or may be provided as a separate display device connected to the ultrasound imaging apparatus 10 in a wire or wireless manner.

The display 150 may include, for example, a liquid crystal display (LCD), a light-emitting diode (LED) display, an organic light-emitting diode (OLED) display, a microelectromechanical system (MEMS) display, or an electronic paper display. However, the type of display 150 is not limited to the above examples, and the display 150 may be provided as various types of display capable of displaying an ultrasound image to a user.

The storage 160 according to the embodiment may store various pieces of information required for controlling the ultrasound imaging apparatus 10. For example, the storage 160 may store an ultrasound image generated through the controller 140, information about a rotation time of the driving device 220 for capturing 3D ultrasound images, and information about a rotation time of the driving device 220 according to a photographing protocol.

To this end, the storage 160 may include a nonvolatile memory device, such as a cache, a read only memory (ROM), a programmable ROM (PROM), an erasable programmable ROM (EPROM), an electrically erasable programmable ROM (EEPROM), and a flash memory, a volatile memory device, such as a random access memory (RAM), or other storage media, such as a hard disk drive (HDD), a CD-ROM, and the like, but the storage 160 is not limited thereto, and may be variously implemented as long as it can store various types of information.

In addition, the storage 160 may be a memory implemented as a chip separated from the processor, which has been described above in connection with the controller 140, or may be implemented as a single chip integrated with the processor.

Meanwhile, the ultrasound imaging apparatus 10 may further include a communicator (not shown). In this case, the communicator may be connected to a network in a wired or wireless manner to communicate with an external device or a server.

The communicator may exchange data with a hospital server or another medical device in a hospital connected through a PACS, and perform data communication according to digital imaging and communications in medicine (DICOM) standard.

In addition, the communicator may perform data communication with a portable terminal of a doctor or a patient, as well as a server or a medical device in a hospital.

The communicator may transmit and receive data related to diagnosis of an object, such as an ultrasound image, echo ultrasound data, and Doppler data of the object through a network, and may also transmit and receive medical images taken by other medical devices, such as computed tomography (CT), magnetic resonance imaging (MRI), and X-ray imaging.

In addition, the communicator may receive information regarding a diagnosis history, a treatment schedule, and the like of a patient from the server, and use the information to diagnose the object.

To this end, the communicator may be connected to a network in a wired or wireless manner to exchange data with a server, a medical device, or a portable terminal. The communicator may include one or more components that enable communication with an external device, and may include, for example, a short range communication module, a wired communication module, and a mobile communication module.

Hereinafter, the determination of the rotation and the position of the transducer module 210 on the basis of the output of the position sensor 240 according to the rotation of the transducer module 210 will be described in detail.

Figure 6:
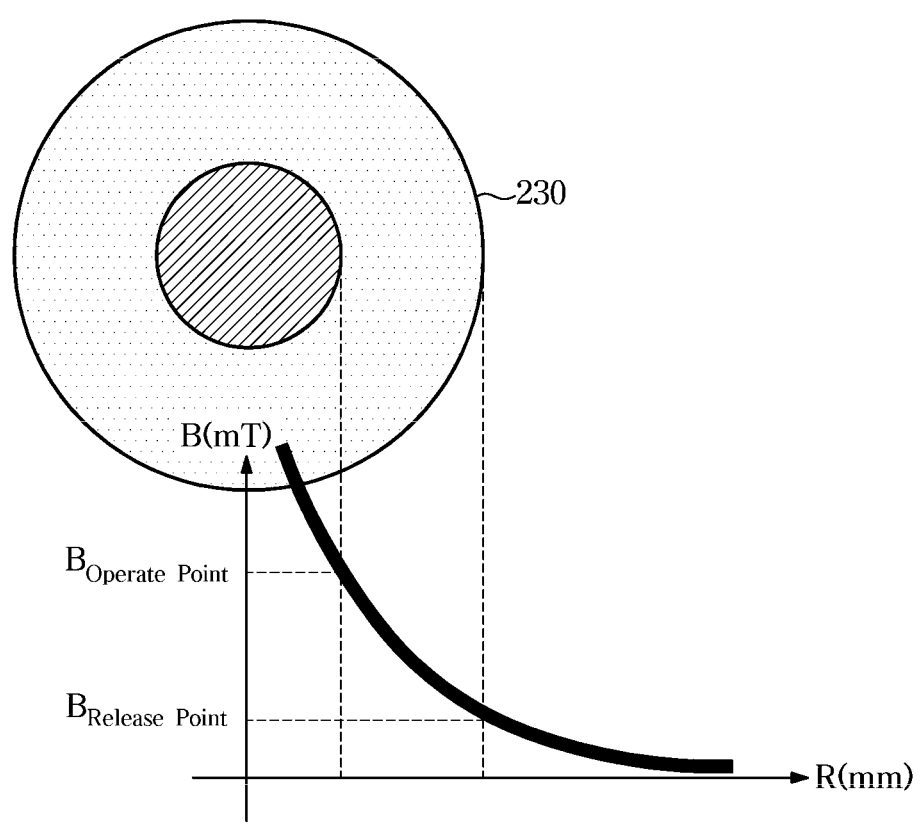
FIG. 6 is a diagram illustrating a magnetic field strength of a magnet according to an embodiment.
Figure 7:
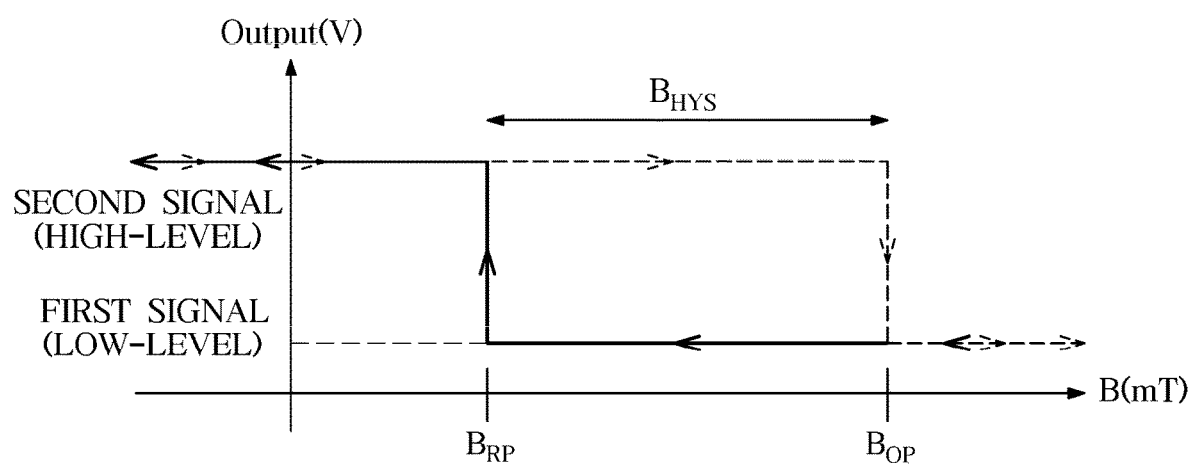
FIG. 7 is a view illustrating hysteresis characteristics of a position sensor according to an embodiment.
Figure 8:
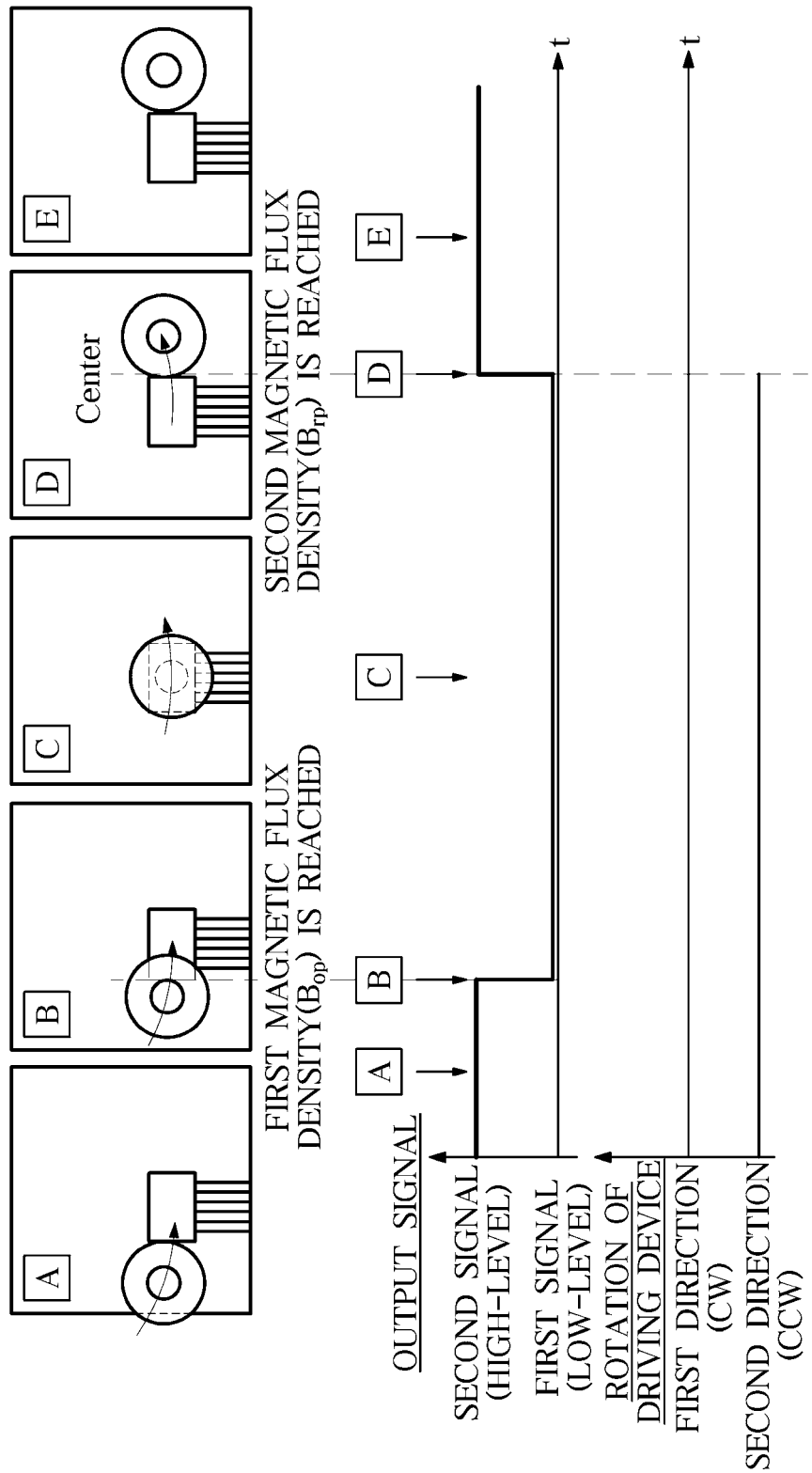
FIG. 8 is a view illustrating an output signal of a position sensor according to rotation of a transducer module according to an embodiment.

FIG. 6 is a diagram illustrating a magnetic field strength of the magnet 230 according to the embodiment, FIG. 7 is a view illustrating hysteresis characteristics of the position sensor 240 according to the embodiment, and FIG. 8 is a view illustrating an output signal of the position sensor 240 according to rotation of the transducer module 210 according to the embodiment.

Referring to FIG. 6, it can be seen that the strength of the magnetic field of the magnet 230 decreases from the central point of the magnet 230 to the surface of the magnet 230.

For example, the strength of the magnetic field of the magnet 230 may exponentially decrease from the central point of the magnet 230 to the surface of the magnet 230.

Accordingly, the magnet 230 may be divided into a central portion having a magnetic field strength greater than or equal to a first magnetic flux density and a peripheral portion having a magnetic field strength less than the first magnetic flux density and greater than or equal to a second magnetic flux density.

In this case, the first magnetic flux density corresponds to a magnetic flux density when the position sensor 240 switches the output signal from the high-level output signal to the low-level output signal as the measured magnetic flux density increases.

In addition, the second magnetic flux density corresponds to a magnetic flux density when the position sensor 240 switches the output signal from the low-level output signal to the high-level output signal as the measured magnetic flux density decreases.

As shown in FIG. 7, when the magnetic flux density reaches $B_{op(operate\ point)}$ as the measured magnetic flux density increases, the position sensor 240 switch the output signal from a second signal (a high-level output signal) to a first signal (a low-level output signal), and when the magnetic flux density reaches a $B_{rp(release\ point)}$ as the measured magnetic flux density decreases, switches the output signal from the first signal to the second signal.

In this case, the first magnetic flux density at which the second signal is switched into the first signal and the second magnetic flux density at which the first signal is switched into the second signal are different from each other due to the hysteresis characteristics of the position sensor 240. That is, the magnitude of the magnetic field strength between the first magnetic flux density and the second magnetic flux density may correspond to $B_{HYS(hysteresis)}$.

Accordingly, the first magnetic flux density may correspond to $B_{op(operate\ point)}$ of the position sensor 240, and the second magnetic flux density may correspond to $B_{rp(release\ point)}$ of the position sensor 240.

The ultrasound imaging apparatus 10 may determine rotation and position of the transducer module 210 on the basis of the above-described characteristics of the magnet 230 and the position sensor 240.

In detail, referring to FIG. 8, the position sensor 240 according to the embodiment may output one of the first signal and the second signal based on the magnet 230 passing through the position sensor 240 as the transducer module 210 rotates.

Hereinafter, for the sake of convenience in description, it is assumed that the position sensor 240 measures the magnetic flux densities on the basis of side edges of the position sensor 240. That is, the position sensor 240 may measure magnetic flux densities of different magnitudes according to portions of the magnet 230 positioned at the side edges of the position sensor 240.

The position sensor 240, in a case that the driving device 220 is driven in the second direction (CCW) to rotate the transducer module 210 in the second direction (CCW), may switch the output signal from the second signal to the first signal when the magnetic flux density reaches the first magnetic flux density $B_{op}$ (point B) as the magnet 230 moves toward the position sensor 240 and may switch the output signal from the first signal to the second signal when the magnetic flux density reaches the second magnetic flux density $B_{rp}$ (point D) as the magnet 230 moves away from the position sensor 240.

The controller 140 according to the embodiment may determine the position of the transducer module 210 on the basis of the switching point of the output signal of the position sensor 240. In detail, the controller 140 may determine the position of the magnet 230 on the basis of the switching point of the output signal of the position sensor 240, and may determine the position of the transducer module 210 on the basis of the rotating direction of the driving device 220 and the position of the magnet 230. To this end, information about the position of the transducer module 210 corresponding to the rotating direction of the driving device 220 and the position of the magnet 230 may be stored in the storage 160 in the design stage.

Hereinafter, a backlash between the transducer module 210 and the driving device 220 and a delay occurring due to the backlash will be described in detail.

Figure 9:
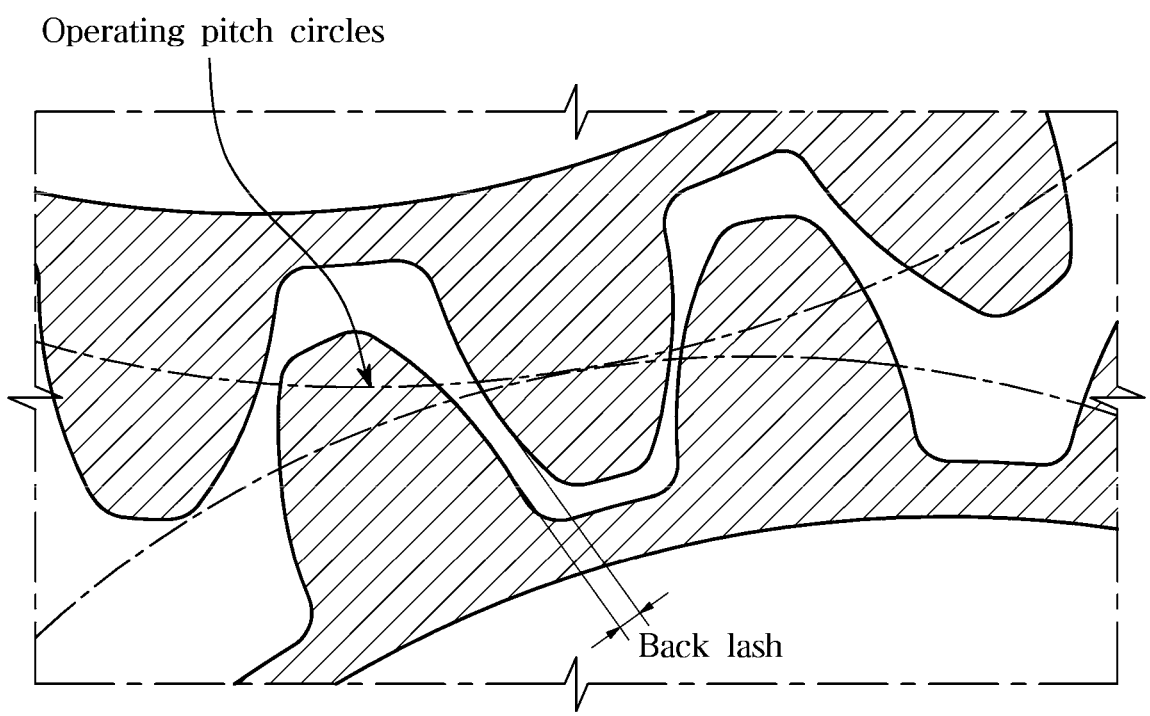
FIG. 9 is a view illustrating a backlash according to an embodiment.
Figure 10:
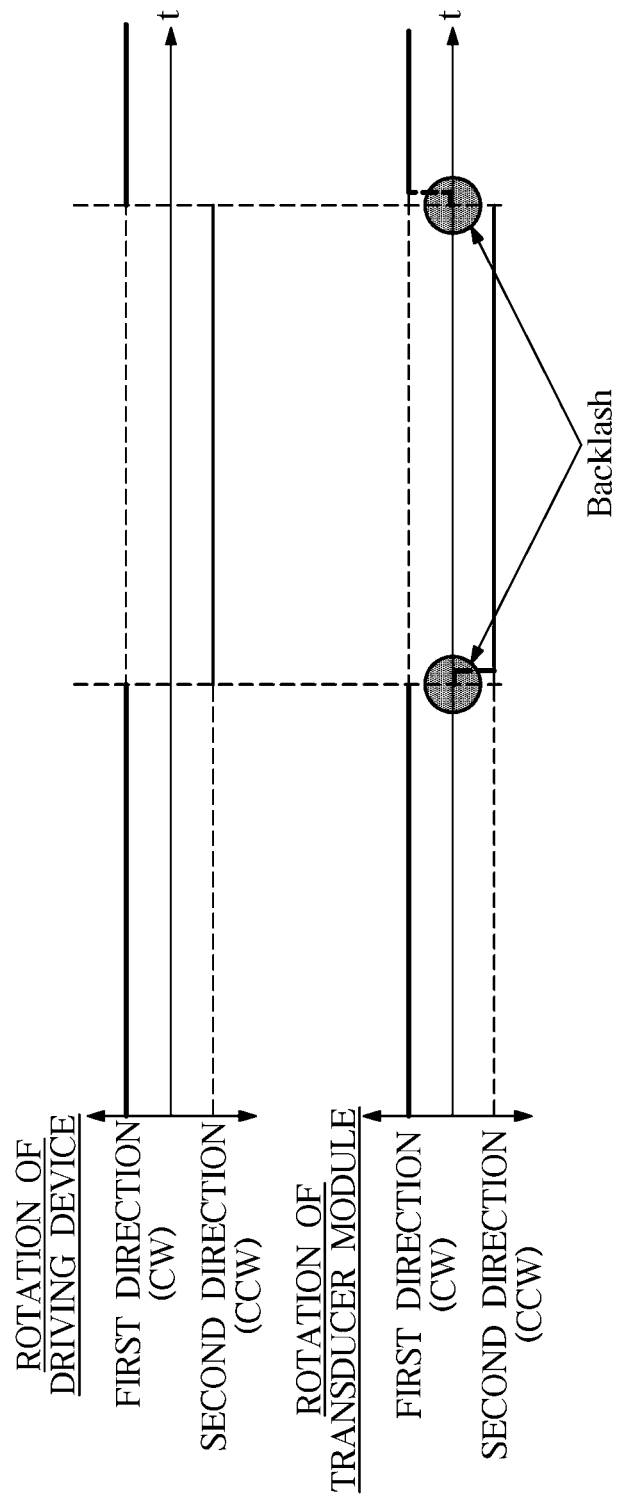
FIG. 10 is a diagram illustrating a backlash value between a transducer module and a driving device according to an embodiment.

FIG. 9 is a view illustrating a backlash according to the embodiment, and FIG. 10 is a diagram illustrating a backlash value between the transducer module 210 and the driving device 220 according to the embodiment.

A backlash refers to an interval between a pair of gears required for smoothly rotating the pair of gears. As shown in FIG. 9, in order for the gears to be engaged with and rotated relative to each other, an upper gear and a lower gear need to be engaged at a regular interval to smoothly operate.

In this case, when the backlash is too small, the interval for the gears to be engaged and rotated is not sufficiently secured, so that a friction between the gears increases due to insufficient lubrication, which may cause gear breakage or malfunction. In contrast, when the backlash is too large, the gears are not sequentially engaged and rotated, which causes the gears to be dislocated or dropped, which causes a difficulty in a smooth rotation operation.

As such, a proper backlash is required for the rotation of the gears. However, when the backlash changes compared to the initial state, the gears may have an operation error, and thus such a phenomenon needs to be prevented.

In other words, a backlash may represent a delay occurring when the rotational movement of the motor 221 of the driving device 220 is transmitted to the transducer module 210.

As the use time of the ultrasound imaging apparatus 10 increases, the backlash between the transducer module 210 and the driving device 220 may increase on the basis of change of characteristics, such as wear or deterioration, and thus, the transduce module 210 may not rotate in accordance with rotation of the driving device 220 but rotate after a predetermined time delay.

In detail, as shown in FIG. 10, when the driving device switches the direction of the output rotational force, the transducer module 210 does not immediately switches the direction in accordance with the switching of the direction of the driving device 220 but perform the direction switching after a certain time. In this case, the delay corresponding to a time taken for the transducer module 210 to start switching the direction after the driving device 220 switches the direction is caused by the backlash between the transducer module 210 and the driving device 220. The delay time may be defined as a backlash value.

In the result, the backlash between the transducer module 210 and the driving device 220 may change as the use time of the ultrasound imaging apparatus 10 increases, and such a change in the backlash value may cause shaking in the acquired ultrasound image.

In detail, the ultrasound imaging apparatus 10 may synthesize an image (a CW image) received in a clockwise direction and an image (a CCW image) received in a counterclockwise direction when the transducer module 210 rotates clockwise and counterclockwise, to implement a first ultrasound image.

In this case, when the speed of the ultrasound waves transmitted in the clockwise direction or counterclockwise direction is delayed due to the backlash, the received two images do not overlap properly, which may result in image shaking.

Accordingly, in order to acquire an ultrasound image without shaking, there is need to determine a backlash value for the ultrasound probe 200 and compensate for the backlash value.

Hereinafter, the determination of the backlash value on the basis of the backlash between the transducer module 210 and the driving device 220 will be described in detail.

Figure 11:
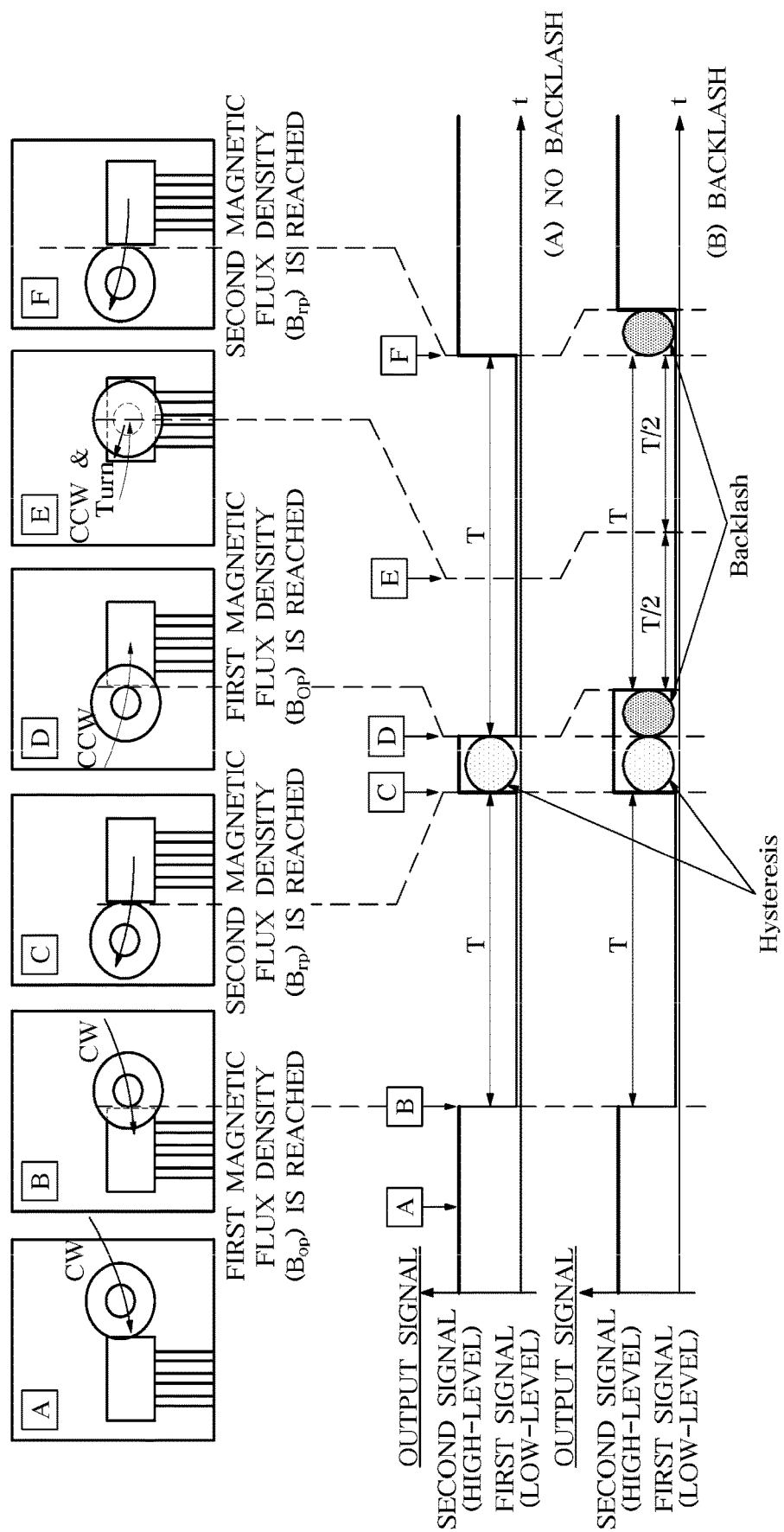
FIGS. 11 and 12 are views illustrating a case in which an ultrasound imaging apparatus determines a backlash value according to an embodiment.
Figure 12:
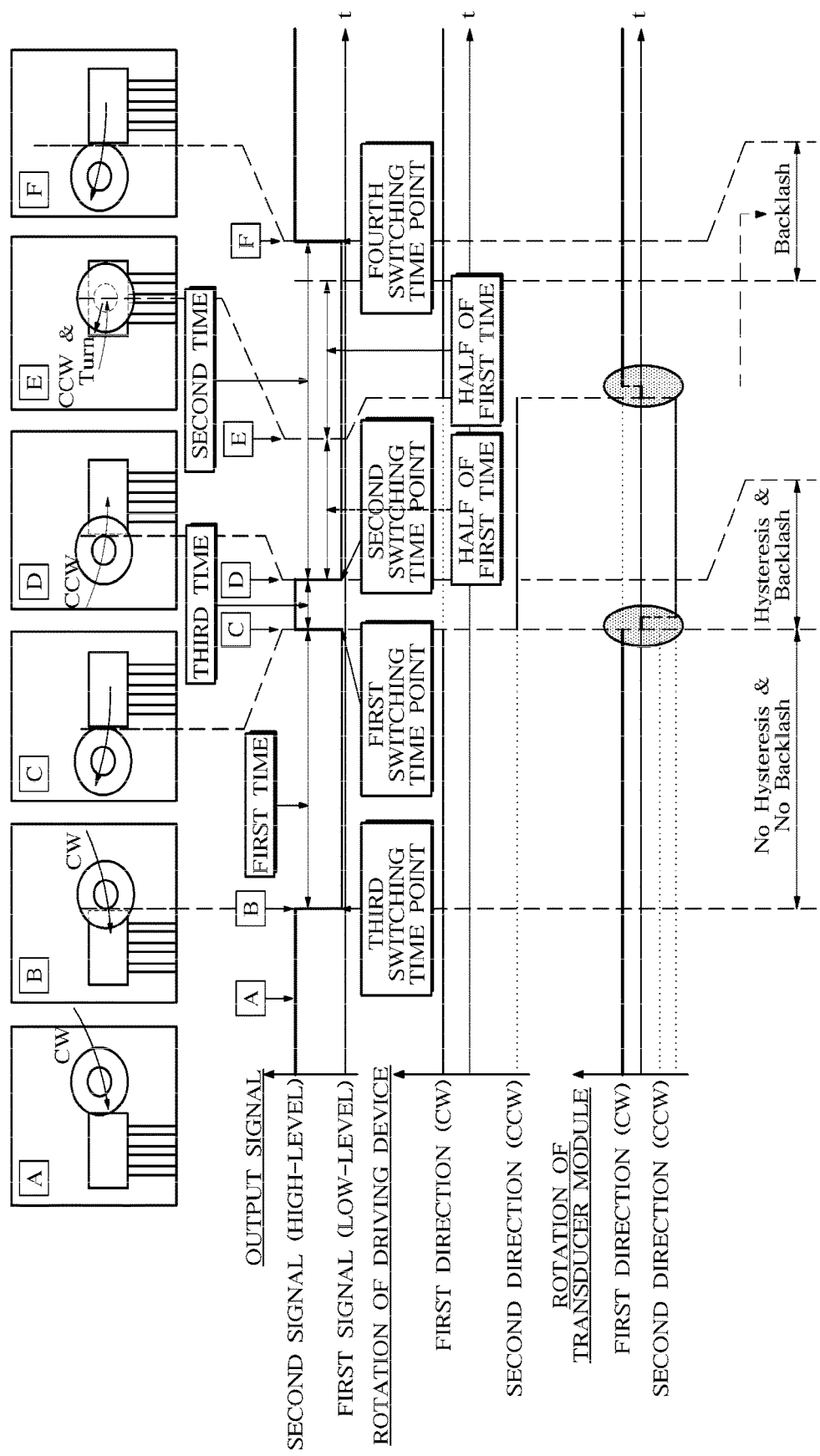

FIGS. 11 and 12 are views illustrating a case in which the ultrasound imaging apparatus 10 determines a backlash value according to the embodiment.

Referring to FIG. 11, before generating an ultrasound image, the controller 140 may control the driving apparatus 220 to rotate the transducer module 210 in a preset pattern to determine a delay time due to a backlash on the transducer module 210 and the driving device 220, that is, a backlash value.

The controller 140 may control the driving device 220 to rotate the transducer module 210 in a preset pattern. In the preset pattern, the transducer module 210 rotates in the first direction (from point A to point C), and at a point (point C) where the magnet 230 passes through the position sensor 240, switches the direction into the second direction.

That is, the controller 140 may control the driving device 220 to rotate the transducer module 210 in the second direction when the magnetic flux density reaches the second magnetic flux density (point C) as the magnet 230 moves away from the position sensor 240 due to the transducer module 210 rotating in the first direction.

In this case, the position sensor 240 may output the second signal (a high-level output signal) until the central portion of the magnet 230 reaches the position sensor 240 after the transducer module 210 switches the direction into the second direction, that is, until the magnetic flux density by the magnet 230 reaches the first magnetic flux density $B_{op}$ (point D).

In this case, as shown in FIG. 11, the time period of outputting the second signal depends on the hysteresis characteristic of the position sensor 240, and may include an error time due to the hysteresis characteristic.

In addition, when a backlash exists between the transducer module 210 and the driving device 220 (FIG. 11B), unlike a case of having no backlash between the transducer module 210 and the driving device 220 as shown in FIG. 11A, the transducer module 210 may switch the direction after a certain period of delay without according with the direction switching of the driving device 220, and thus the time period of outputting the second signal may include a backlash value.

Subsequently, in a case that the magnet 230 enters an area within the low-level output range of the position sensor 240 (after point D), the transducer module 210 may switch the direction one or more times during a time corresponding to the first time T taken for the magnet 230 to pass through the position sensor 240 as a result of the transducer 210 rotating in the first direction. In this case, the magnet 230 is positioned within the low-level output range of the position sensor 240.

In this case, the low-level output range of the position sensor 240 may correspond to a range from a point at which the magnetic flux density reaches the first magnetic flux density $B_{op}$ as the magnet 230 moves toward the position sensor 240 to a point before the magnetic flux density reaches the second magnetic flux density $B_{rp}$ as the magnet 230 moves away from the position sensor 240.

In addition, the first time is a period of time in which the magnet 230 moves toward the position sensor and then moves away from the position sensor 240 while the transducer module 210 is moving in the first direction (from point B to point C), that is, a time taken for the magnet 230 to pass through the low-level output range of the position sensor 240 (from point B to point C).

For example, as shown in FIG. 11, the transducer module 210 may perform direction switching one time during a time corresponding to the first time T. In addition, as shown in FIG. 11, the transducer module 210 may maintain the same rotational direction for a time corresponding to half of the first time before and after a point (point E) at which the direction is switched.

In a case that no backlash exists between the transducer module 210 and the driving device 220 (FIG. 11A), the magnet 230 passes through the position sensor 240 according to the transducer module 210 rotating at the same angular speed regardless of the rotating direction during the time corresponding to the first time T, and the position sensor 240 may accordingly switch the output signal from the first signal to the second signal.

However, in a case that a backlash exists between the transducer module 210 and the driving device 220 (FIG. 11B), a delay time occurs in proportion to the number of times the transducer module 210 is switched in the direction during the time corresponding to the first time (T). Accordingly, the magnet 230 may pass through the position sensor 240 after further rotating by the delay time. In this case, the backlash value may correspond to a delay time according to one turn of directional switch, and may be determined by dividing the total delay time by the number of times the direction switching is performed.

In this case, the position sensor 240 may switch the output signal from the first signal to the second signal at a point (F point) rotated by the transducer module 210 as much as the backlash value, with respect to the switching point when no backlash exists between the transducer module 210 and the driving device 220.

In other words, when a backlash exists between the transducer module 210 and the driving device 220, the transducer module 210 may further rotate until the magnetic flux density reaches the second magnetic flux density (point F), as a result of the magnet 230 moving away from the position sensor 240 after the first time T, that is, until the magnet 230 deviates from the low-level output range of the position sensor 240.

The controller 140 may determine the second time for which the magnet 230 stays within the low-level output range of the position sensor 240 after the transducer module 210 switches the direction into the second direction, and determine the backlash value on the basis of the difference value between the first time taken for the magnet 230 to pass through the position sensor 240 as a result of the transducer module 210 rotating in the first direction and the determined second time.

Hereinafter, referring to FIG. 12, the determining of the backlash value will be described from the perspective of the controller 140 in more detail.

The controller 140 may determine the first time for which the first signal is output as a result of the transducer module 210 rotating in the first direction.

In this case, the controller 140, from a point in time (a third switching time point) when the output signal of the position sensor 240 is switched from the second signal to the first signal to a point in time (a first switching time point) when the output signal is switched into the second signal again as the magnet 230 moves toward and passes through the position sensor 240, controls the transducer module 210 to rotate in the first direction That is, the controller 140 may control the driving device 220 to switch the rotating direction of the transducer module 210 from the first direction to the second direction at the first switching time point where the output signal of the position sensor 240 is switched from the first signal to the second signal.

In this case, the controller 140 may determine the third switching time point at which the output signal is switched from the second signal to the first signal as the magnet 230 moves toward the position sensor 240 due to the transducer module 210 rotating in the first direction, and determine the time difference between the third switching time point and the first switching time point as the first time.

The controller 140 may control the driving device 220 to switch the rotating direction of the transducer module 210 one or more times during a time corresponding to the first time with respect to the second switching time point at which the output signal is switched from the second signal to the first signal after the first switching time point.

In this case, the number of times the rotating direction is switched during the time corresponding to the first time is not limited, and for example, as shown in FIG. 12, one time of switching may be performed.

However, in order to generate a delay time corresponding to a backlash value according to the switching of the rotating direction. the controller 140 may control the driving device 220 to rotate the transducer module 210 in the same direction within a preset time from a point in time at which the rotating direction of the transducer module 210 is switched, during a time corresponding to the first time with respect to the second switching time point.

In this case, the preset time may be set in the design stage to have a length longer than the delay time due to the backlash between the transducer module 210 and the driving device 220 and stored in the storage 160, or may be set by the user through the inputter 130 and stored in the storage 160.

The controller 140 may determine the second time for which the first signal is output after the second switching time point.

In detail, the controller 140 may control the driving device 220 to rotate the transducer module 210 until a fourth switching time point, at which the position sensor 240 switches the output signal from the first signal to the second signal, after a time corresponding to the first time.

In other words, the controller 140 may determine the fourth switching time point at which the output signal is switched from the first signal to the second signal as the magnet 230 moves away from the position sensor 240 due to rotation of the transducer module 210, after a time corresponding to the first time from the second switching time point, and may determine the time difference between the second switching time point and the fourth switching time point as the second time.

Thereafter, the controller 140 may determine a backlash value on the basis of the difference value between the first time and the second time.

In detail, the controller 140 may determine the backlash value by dividing the difference between the first time and the second time and the second switching time by the number of times the rotating direction of the transducer module 210 is switched during a time corresponding to the first time with respect to the second switching time point.

As described above, the ultrasound imaging apparatus 10 may determine the backlash value generated by the backlash between the transducer module 210 and the driving device 220 by rotating the transducer module 210 according to a predetermined pattern.

In this case, when controlling the driving device 220 to determine the backlash value, the controller 140 may control the motor of the driving device 220 to rotate at a preset speed such that the driving device 220 transmits a constant rotational force to the transducer module 210 and thus the transducer module 210 rotates at a constant speed.

In this case, the preset speed may be preset in the design stage and stored in the storage 160, or may be adjusted by the user through the inputter 130 according to embodiments.

In addition, the operation for determining the backlash value may be performed before the ultrasound signal is irradiated onto the object, that is, before the ultrasound image is taken.

In detail, the controller 140 may determine the backlash value by controlling the driving device 220 of the ultrasound probe 200 at a time point when the ultrasound probe 200 is connected to the main body 100 of the ultrasound imaging apparatus 10 such that the transducer module 210 rotates in a preset pattern.

In this case, the connecting of the ultrasound probe 200 to the main body 100 may include initially connecting the ultrasound probe 200 to the main body 100 in a wired or wireless manner, and activating the previously connected ultrasound probe 200 by a user's selection to be used.

In addition, according to an embodiment, the controller 140 may determine the backlash value by controlling the driving device 220 of the ultrasound probe 200 to rotate the transducer module 210 in a preset pattern in response to receiving an input for photographing a 3D ultrasound image through rotation of the transducer module 210 or receiving an input for determining the backlash value from the user through the inputter 130.

In addition, according to an embodiment, the controller 140 may determine the backlash value by controlling the driving device 220 of the ultrasound probe 200 at a predetermined time interval to rotate the transducer module 210 in a preset pattern.

In addition, the controller 140 according to the embodiment may control the display 150 to output a notification, or may control the ultrasound probe 200 to re-determine the backlash value such that the backlash value is re-determined when the determined backlash value exceeds a preset threshold value.

In this case, the preset threshold value may be a value corresponding to a backlash value that is too large to be compensated for, and may be preset in the design stage and stored in the storage 160.

In addition, the controller 140 according to the embodiment may generate a shaking-free ultrasound image by compensating for the determined backlash value.

Hereinafter, the generation of the shaking-free ultrasound image by compensating for the backlash value will be described in detail.

Figure 13:
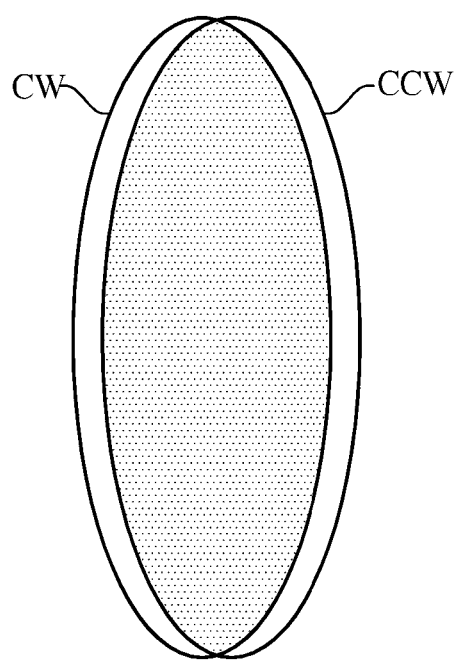
FIG. 13 is a view illustrating a case in which an ultrasound imaging apparatus compensates for a determined backlash value according to an embodiment.
Figure 13:
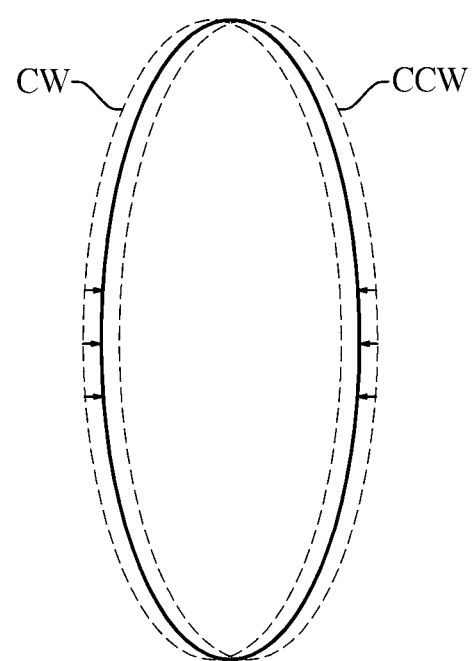

FIG. 13 is a view illustrating a case in which the ultrasound imaging apparatus 10 compensates for the determined backlash value according to the embodiment.

Referring to FIG. 13, the controller 140 may synthesize an image (a CW image) received in a clockwise direction and an image (a CCW image) received in a counterclockwise direction when the transducer module 210 rotates clockwise and counterclockwise, to implement a first ultrasound image.

In this case, as shown in FIG. 13A, when the speed of the ultrasound wave transmitted in the clockwise or counterclockwise direction may be delayed due to the backlash, the received two images do not overlap properly, which may result in image shaking.

That is, in FIG. 13A, when the circle on the left is an image received in a clockwise direction, and the circle on the right is an image received in a counterclockwise direction, the circles do not overlap each other, causing the ultrasound image to be shaken.

The image shaking is a phenomenon caused by a backlash, and occurs when the transducer module 210 needing to be rotated by the rotation of the driving device 220 in the same direction as the driving device 220 fails to rotate in accordance with the rotation of the driving device 220.

For example, when the motor 221 of the driving device 220 rotates in a clockwise direction and then rotates in a counterclockwise direction, a delay occurs in which the transducer module 210 does not immediately rotate to correspond with the switching, and thus a backlash value as much as the delay interval is generated, and the arrangement axis (the central axis) of the driving device 220 and the transducer module 210 does not coincide with the initial axis, so that the clockwise image and the counterclockwise image do not match with respect to the central axis, thereby causing the image shaking.

Accordingly, the controller 140 may generate a rendering image of the ultrasound image by shifting a rendering image corresponding to the clockwise direction and a rending image corresponding to the counterclockwise direction by an angle corresponding to the backlash value in the direction corresponding thereto with respect to the central axis of the transducer module 210.

In detail, the controller 140 may correct the image shaking by shifting the clockwise image (CW) and the counterclockwise image (CCW), which do not match each other, to a degree delayed by the backlash with respect to the central axis through the image correction. That is, the shaking is eliminated by matching the clockwise image and the counterclockwise image.

That is, the calculated backlash value is expressed in units of time t, so that the distance by which the transducer module 210 due to the backlash is delayed is identified on the basis of the backlash value using the backlash value and the speed v of the motor 221 of the driving device 220, that is, the increased angle is identified, and the controller 140 may perform image correction to correspond to the delayed value when rendering the ultrasound image.

Hereinafter, a case of rendering a single image using a clockwise rendering image and a counterclockwise rendering image is described in brief. For example, a single 3D image is generated by arranging 50 clockwise cross-sectional images, and a single 3D image is generated by arranging 50 clockwise cross-sectional images, and the images are combined and rendered as a single image.

In this case, the controller 140 may allow the clockwise image and the counterclockwise image delayed by the backlash to be shifted by the amount of the delay, to generate a shaking-free image. That is, the controller 140 corrects the image by offsetting the amount shaken due to the backlash.

As for the period or the time point of correcting the rendering image, the correcting may be performed at all times using a backlash value calculated in real time, or may be performed by setting a predetermined period or duration.

In addition, the controller 140 may compensate for the backlash value by controlling the driving device 220.

In detail, when controlling the driving device 220 to switch the rotating direction of the transducer module 210 to take an ultrasound image by irradiating an ultrasound signal to an object, the controller 140 may control the driving device 220 to output the rotational force in the same direction for a time extended by a time corresponding to the backlash value from a preset time.

In this case, the preset time may correspond to a time that is set for the transducer module 210 to rotate after switching the direction such that a rotation angle determined according to a photographing protocol is provided. By compensating for the rotation time of the transducer module 210 using the time extended by the time correspond to the backlash value from the preset time as described above, the transducer module 210 may be prevented from rotating an angle less than a desired rotation angle due to the backlash value.

As described above, the ultrasound imaging apparatus 10 determines the delay time generated on the basis of the backlash between the transducer module 210 and the driving device 220, i.e., the backlash value, and compensates for the determined backlash value, thereby providing the ultrasound wave free of shaking.

In addition, the ultrasound imaging apparatus 10 may determine an error time due to the hysteresis characteristic of the position sensor 240 and compensate for the error time.

Hereinafter, the determination of the error time due to the hysteresis characteristic of the position sensor 240 will be described in detail.

Figure 14:
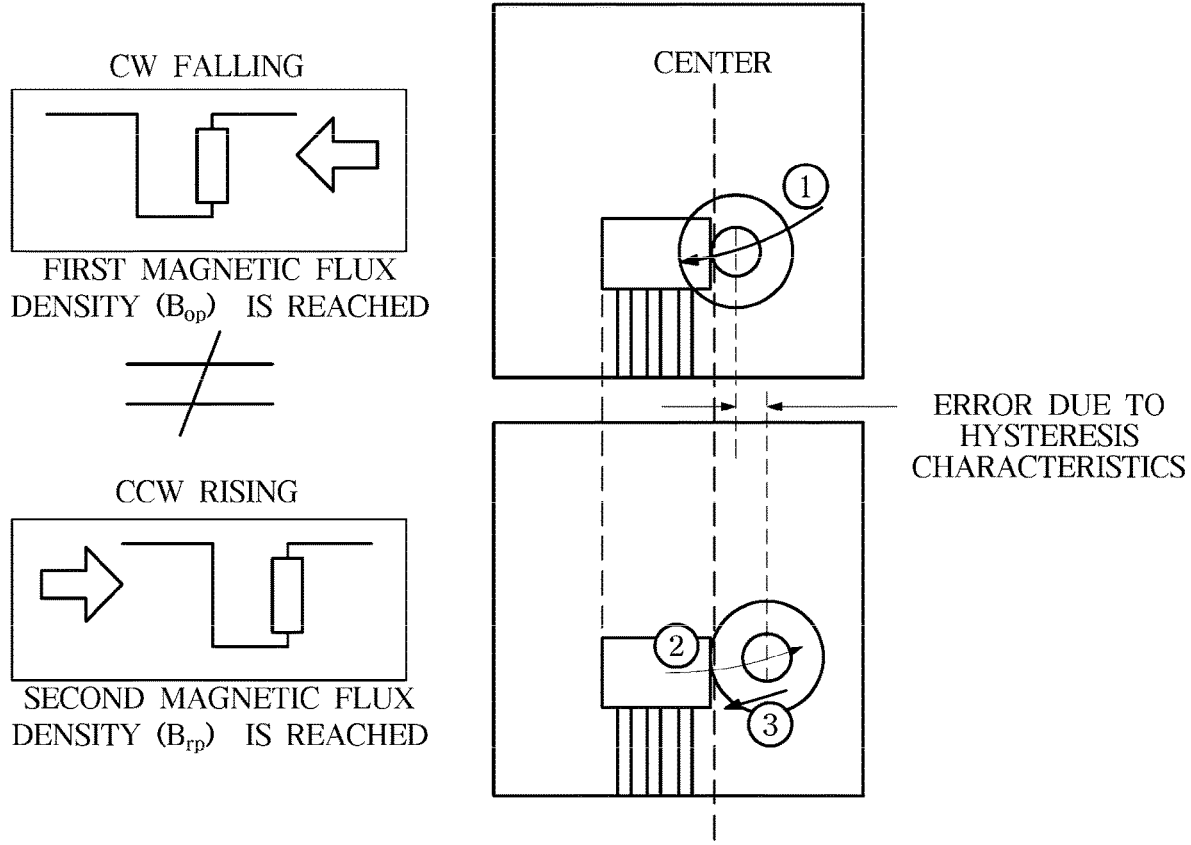
FIG. 14 is a view illustrating a case in which an ultrasound imaging apparatus compensates for an error due to hysteresis characteristics of a position sensor.

FIG. 14 is a view illustrating a case in which the ultrasound imaging apparatus 10 compensates for an error due to hysteresis characteristics of the position sensor 240.

Referring to FIG. 14, the controller 140 may determine an error time due to hysteresis characteristics of the position sensor 240 and compensate for the error time.

In detail, when controlling the transducer module 210 to rotate in a predetermined pattern, the controller 140 may determine a time from a point in time at which the magnet 230 passes through the position sensor 240 as a result of the transducer module 210 rotating in the first direction to a point in time at which the magnet 230 enters the low-level output range of the position sensor 240 as a result of the transducer module 210 switching the direction into the second direction as a third time, and may determine a difference value between the third time and the backlash value as an error time due to the hysteresis characteristic.

That is, as shown in FIG. 12, the controller 140 may determine the time difference between the first switching time point and the second switching time point as the third time, and determine a time shortened by a time corresponding to the backlash value from the third time as the error time due to the hysteresis characteristic of the position sensor 240.

The controller 140 may control the transducer module 210 such that the transducer module 210 is positioned on the central axis of the rotation radius for the ultrasound image capturing. In this case, the controller 140 may set a point (CW falling) at which the output signal of the position sensor 240 is switched from the high-level output signal to the low-level output signal as a result of the transducer module 210 rotating in the first direction ($\hat{1}$) as the central axis of the transducer module 210, and store the point (CW falling) in the storage 160.

In this case, when the controller 140 determines a point (CCW Rising) at which the output signal of the position sensor 240 is switched from the low-level output signal to the high-level output signal as a result of the transducer module 210 rotating in the second direction ($\hat{2}$) as the central axis of the transducer module 210, a difference occurs between the set central axis and the determined central axis due to the hysteresis characteristic of the position sensor 240.

Accordingly, the controller 140 may determine a point $\hat{3}$ rotated in the first direction by the error time from the point (CCW rising) at which the output signal of the position sensor 240 is switched from the low-level output signal to the high-level output signal as a result of the transducer module 210 rotating in the second direction, as the central axis of the transducer module 210.

That is, the ultrasound imaging apparatus 10 compensates for an error time that may occur due to the hysteresis characteristic of the position sensor 240, so that the transducer module 210 may be positioned on the same central axis regardless of the direction in which the transducer module 210 rotates.

Hereinafter, a method of controlling the ultrasound imaging apparatus 10 according to an embodiment will be described. The ultrasound imaging apparatus 10 according to the above-described embodiment may be applied to the method of controlling the ultrasound imaging apparatus 10 to be described below. Therefore, the description made above with reference to FIGS. 1 to 14 may be equally applied to the method of controlling the ultrasound imaging apparatus 10 according to the embodiment unless otherwise mentioned.

Figure 15:
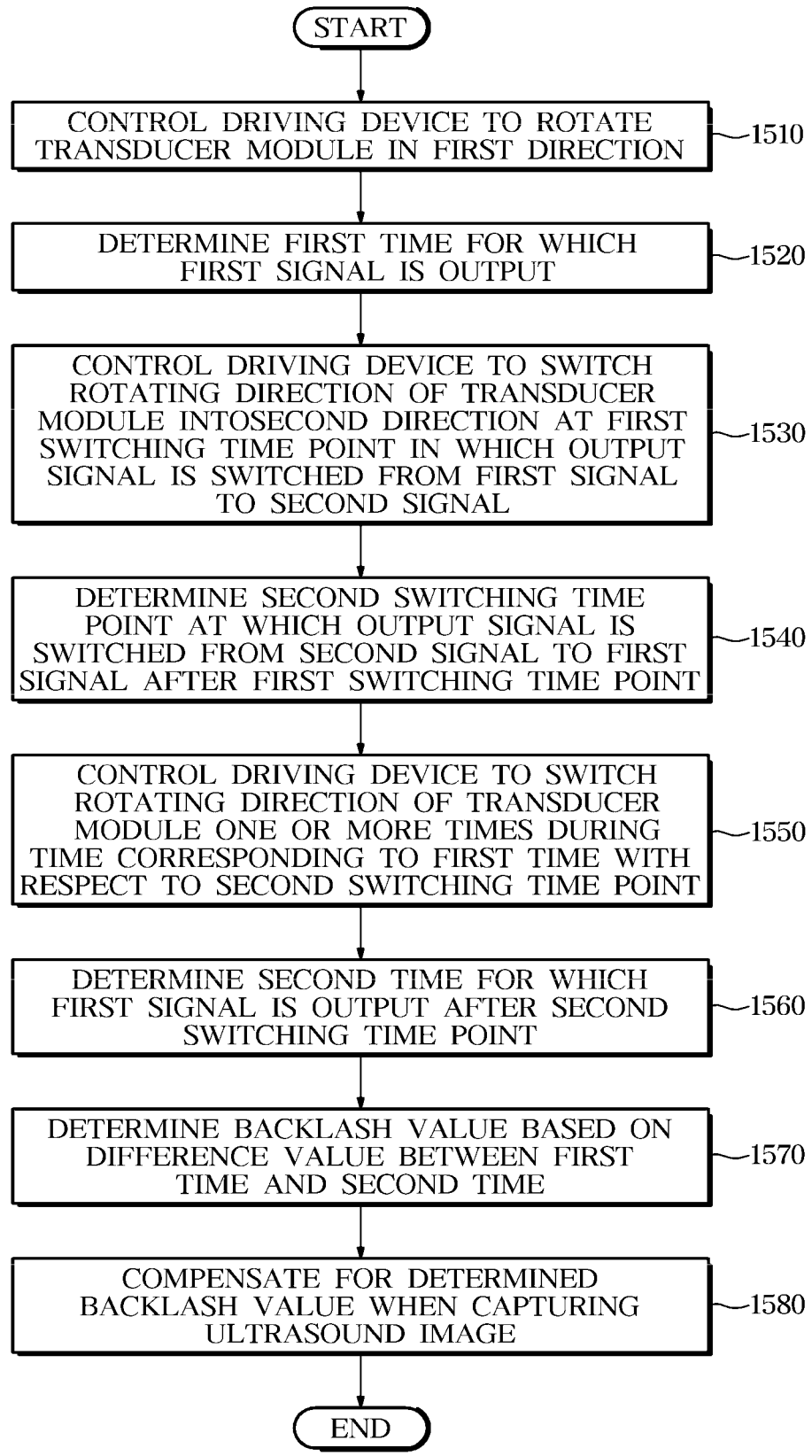
FIG. 15 is a flowchart showing a case in which a backlash value is determined by a method of controlling an ultrasound imaging apparatus according to an embodiment.

FIG. 15 is a flowchart showing a case in which a backlash value is determined by a method of controlling the ultrasound imaging apparatus 10 according to an embodiment.

Referring to FIG. 15, the controller 140 according to the embodiment may control the driving device 220 to rotate the transducer module 210 in the first direction (1510), and may determine the first time for which the first signal is output (1520).

That is, the controller 140 may determine the first time for which the first signal is output as the transducer module 210 rotates in the first direction.

In this case, the controller 140, from a point in time (a third switching time point) when the output signal of the position sensor 240 is switched from the second signal to the first signal to a point in time (a first switching time point) when the output signal is switched into the second signal again as the magnet 230 moves toward and passes through the position sensor 240, controls the transducer module 210 to rotate in the first direction.

In addition, the controller 140 may control the driving device 220 to switch the rotating direction of the transducer module 210 into the second direction at the first switching time point in which the output signal of the position sensor 240 is switched from the first signal to the second signal (1530).

In this case, the controller 140 may determine the third switching time point at which the output signal is switched from the second signal to the first signal as the magnet 230 moves toward the position sensor 240 due to the transducer module 210 rotating in the first direction, and determine the time difference between the third switching time point and the first switching time point as the first time.

The controller 140 may determine the second switching time point at which the output signal is switched from the second signal to the first signal after the first switching time point (1540), and may control the driving device 220 to switch the rotating direction of the transducer module 210 one or more times during a time corresponding to the first time with respect to the second switching time point (1550).

However, in order to generate a delay time corresponding to a backlash value according to the switching of the rotating direction, the controller 140 may control the driving device 220 to rotate the transducer module 210 in the same direction within a preset time from a point in time at which the rotating direction of the transducer module 210 is switched, during a time corresponding to the first time with respect to the second switching time point In this case, the preset time may be set in the design stage to have a length longer than the delay time due to the backlash between the transducer module 210 and the driving device 220 and stored in the storage 160, or may be set by the user through the inputter 130 and stored in the storage 160.

The controller 140 may determine the second time for which the first signal is output after the second switching time point (1560).

In detail, the controller 140 may control the driving device 220 to rotate the transducer module 210 until a fourth switching time point, at which the position sensor 240 switches the output signal from the first signal to the second signal, after a time corresponding to the first time.

In other words, the controller 140 may determine the fourth switching time point at which the output signal is switched from the first signal to the second signal as the magnet 230 moves away from the position sensor 240 due to rotation of the transducer module 210, after a time corresponding to the first time from the second switching time point, and may determine the time difference between the second switching time point and the fourth switching time point as the second time.

Thereafter, the controller 140 may determine the backlash value on the basis of the difference value between the first time and the second time (1570).

In detail, the controller 140 may determine the backlash value by dividing the difference between the first time and the second time and the second switching time by the number of times the rotating direction of the transducer module 210 is switched during a time corresponding to the first time with respect to the second switching time point.

As described above, the ultrasound imaging apparatus 10 may determine the backlash value generated by the backlash between the transducer module 210 and the driving device 220 by rotating the transducer module 210 according to a predetermined pattern.

In addition, the controller 140 may compensate for the determined backlash value when capturing an ultrasound image (1580).

That is, when controlling the transducer module 210 to rotate while irradiating an ultrasound signal to capture an ultrasound image, the controller 140 may compensate for the determined backlash value.

In detail, when controlling the driving device 220 to switch the rotating direction of the transducer module 210, the controller 140 may control the driving device 220 to output a rotational force in the same direction for a time extended by a time corresponding to the backlash value from a preset time.

In this case, the preset time may correspond to a time that is set for the transducer module 210 to rotate after switching of the direction to provide a rotation angle determined according to a photographing protocol. By compensating for the rotation time of the transducer module 210 using the time extended by the time corresponding to the backlash value from the preset time as described above, the transducer module 210 may be prevented from rotating an angle less than a desired rotation angle due to the backlash value.

In addition, the controller 140 may compensate for the backlash value by acquiring an ultrasound image of each of the clockwise and counterclockwise directions and correcting the ultrasound image corresponding to each of the clockwise and counterclockwise directions.

In detail, the controller 140 may shift each of a rending image corresponding to the first direction and a rendering image corresponding to the second direction in the direction corresponding thereto from the center axis of the transducer module 210 by an angle corresponding to the backlash value, so that a rendering image of the ultrasound image is generated. In this way, the ultrasound imaging apparatus 10 may provide an ultrasound image without shaking.

Figure 16:
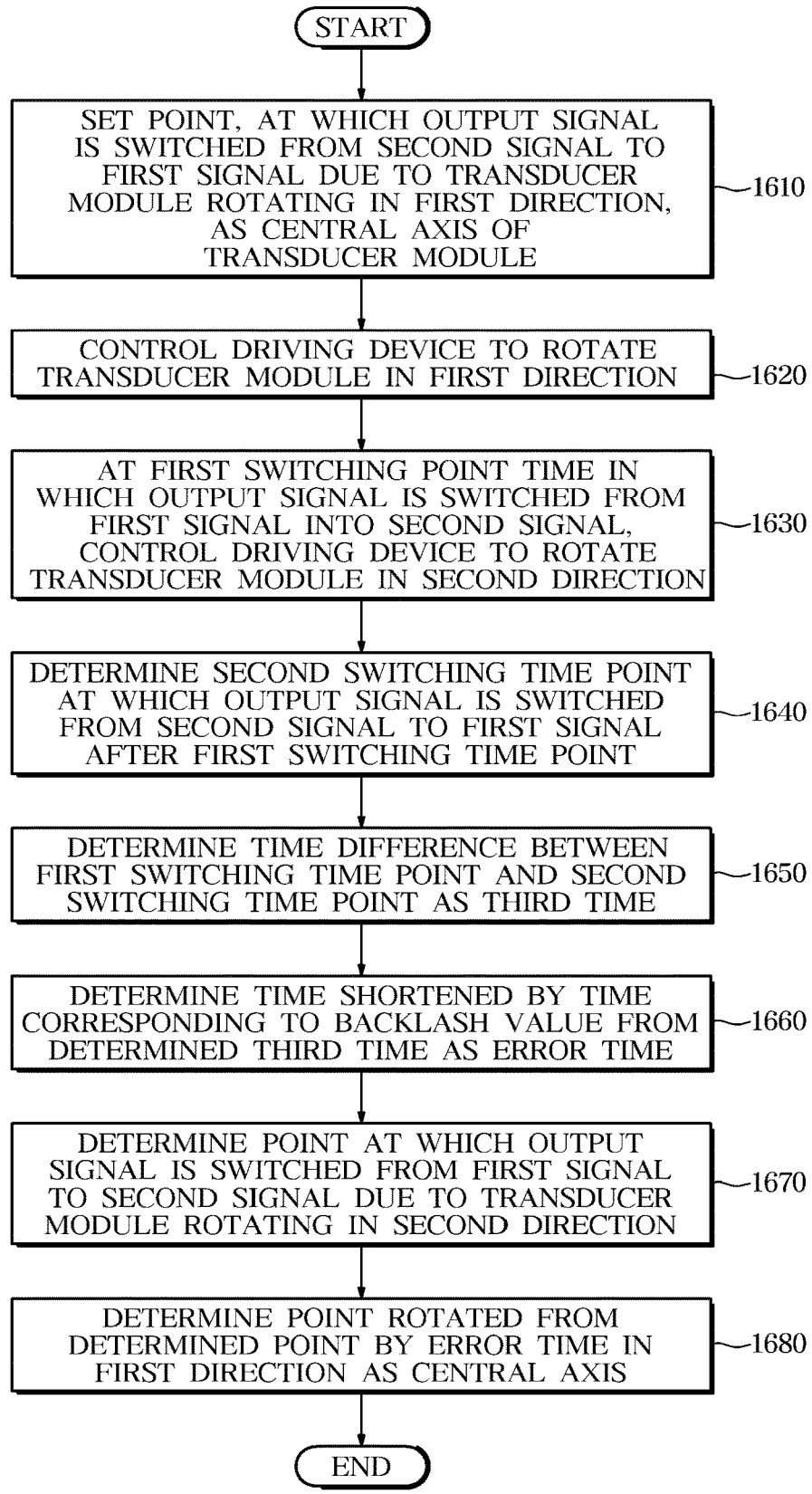
FIG. 16 is a flowchart showing a case in which an error due to hysteresis characteristics of a position sensor is compensated for by a method of controlling an ultrasound imaging apparatus according to an embodiment.

FIG. 16 is a flowchart showing a case in which an error due to hysteresis characteristics of the position sensor 240 is compensated for by a method of controlling an ultrasound imaging apparatus 10 according to an embodiment.

Referring to FIG. 16, the controller 140 may set a point, at which the output signal of the position sensor 240 is switched from the second signal to the first signal as a result of the transducer module 210 rotating in the first direction, as the central axis of the transducer module 210 (1610).

The controller 140 may control the driving device 220 to rotate the transducer module 210 in the first direction (1620), and at the first switching point time in which the output signal is switched from the first signal into the second signal, may control the driving device 220 to switch the direction of the transducer module 210 into the second direction (1630), and may determine the second switching time point at which the output signal is switched from the second signal to the first signal after the first switching time point (1640). Since the description thereof is the same as described above, detailed description thereof will be omitted.

The controller 140 may determine the time difference between the first switching time point and the second switching time point as the third time (1650), and determine a time shortened by a time corresponding to the backlash value from the determined third time as the error time (1660).

In detail, when controlling the transducer module 210 to rotate in a predetermined pattern, the controller 140 may determine a time from a point in time at which the magnet 230 passes through the position sensor 240 as a result of the transducer module 210 rotating in the first direction to a point in time at which the magnet 230 enters the low-level output range of the position sensor 240 as a result of the transducer module 210 switching the direction into the second direction as a third time, and may determine a difference value between the third time and the backlash value as an error time due to the hysteresis characteristic.

In addition, the controller 140 may determine a point at which the output signal is switched from the first signal to the second signal as a result of the transducer module 210 rotating in the second direction (1670), and may determine a point rotated from the determined point by the error time in the first direction as the central axis (1680).

That is, the controller 140 may control the transducer module 210 to be positioned on the central axis of the rotation radius for the ultrasound image capturing. In this case, as described in operation 1610, the controller 140 may set a point (CW falling) at which the output signal of the position sensor 240 is switched from the high-level output signal to the low-level output signal as a result of the transducer module 210 rotating in the first direction as the central axis of the transducer module 210, and store the point (CW falling) in the storage 160.

In this case, when the controller 140 determines a point (CCW rising) at which the output signal of the position sensor 240 is switched from the low-level output signal to the high-level output signal as a result of the transducer module 210 rotating in the second direction as the central axis of the transducer module 210, a difference occurs between the set central axis and the determined central axis due to the hysteresis characteristic of the position sensor 240.

Accordingly, the controller 140 may determine a point rotated by the error time in the first direction from the point (CCW rising) at which the output signal of the position sensor 240 is switched from the low-level output signal to the high-level output signal as a result of the transducer module 210 rotating in the second direction, as the central axis of the transducer module 210.

That is, the ultrasound imaging apparatus 10 compensates for an error time that may occur due to the hysteresis characteristics of the position sensor 240, so that the transducer module 210 may be positioned on the same central axis regardless of the direction in which the transducer module 210 rotates.

Meanwhile, the disclosed embodiments may be embodied in the form of a recording medium storing instructions executable by a computer. The instructions may be stored in the form of program code and, when executed by a processor, may generate a program module to perform the operations of the disclosed embodiments. The recording medium may be embodied as a computer-readable recording medium.

The computer-readable recording medium includes all kinds of recording media in which instructions which may be decoded by a computer are stored, for example, a Read Only Memory (ROM), a Random Access Memory (RAM), a magnetic tape, a magnetic disk, a flash memory, an optical data storage device, and the like.

As is apparent from the above, the ultrasound imaging apparatus and the method of controlling the same can provide a clear ultrasound image by measuring the position of a transducer module on the basis of an output value of a position sensor and compensating for the backlash value.

Although embodiments of the disclosure have been described for illustrative purposes, those skilled in the art will appreciate that various modifications, additions and substitutions are possible, without departing from the scope and spirit of the disclosure. Therefore, embodiments of the disclosure have not been described for limiting purposes.

What is claimed is:

1. An ultrasound imaging apparatus comprising:
    an ultrasound probe including a transducer module including an ultrasound transducer array, a driving device configured to rotate the transducer module, a magnet configured to rotate as a result of rotation of the transducer module, and a position sensor configured to output one of a first signal and a second signal on the basis of a change in magnetic flux density according to rotation of the magnet; and
    a controller configured to determine a first time for which the first signal is output as the transducer module rotates in a first direction, to control the driving device to switch a rotating direction of the transduce module from the first direction to a second direction at a first switching time point at which an output signal is switched from the first signal to the second signal, to control the driving device to switch the rotating direction of the transducer module during a same time as the first time, starting from a second switching time point at which the output signal is switched from the second signal to the first signal after the first switching time point, to determine a second time for which the first signal is output after the second switching time point, and to determine a backlash value on the basis of a difference value between the first time and the second time,
    wherein the position sensor switches the output signal from the second signal to the first signal when the magnetic flux density reaches a first magnetic flux density as the magnet moves toward the position sensor, and switches the output signal from the first signal to the second signal when the magnetic flux density reaches a second magnetic flux density as the magnet moves away from the position sensor, wherein the first signal and the second signal are different from each other due to the position sensor's hysteresis characteristics, and
    wherein the controller determines a third switching time point, which is a time point before the first switching time point, at which the output signal is switched from the second signal to the first signal as the magnet moves toward the position sensor as a result of the transducer module rotating in the first direction, and determines a time difference between the third switching time point and the first switching time point to be the first time.

2. The ultrasound imaging apparatus of claim 1, wherein the controller determines the backlash value by dividing the difference value between the first time and the second time by a number of times the rotating direction of the transducer module is switched during the same time as the first time, starting from the second switching time point.

3. The ultrasound imaging apparatus of claim 1, wherein the controller controls the driving device to rotate the transducer module in one of the first direction and the second direction within a preset time from the second switching time point at which the rotating direction of the transducer module is switched, during the same time as the first time, starting from the second switching time point.

4. The ultrasound imaging apparatus of claim 1, wherein the controller determines a fourth switching time point, which is a time point after the second switching time point, at which the output signal is switched from the first signal to the second signal as the magnet moves away from the position sensor as a result of the rotating of the transducer module after the same time as the first time, starting from the second switching time point, and determines a time difference between the second switching time point and the fourth switching time point as the second time.

5. The ultrasound imaging apparatus of claim 1, wherein the driving device further includes:
    a motor configured to generate a rotating power for rotating the transducer module; and
    a transmission device configured to transmit the rotary power of the motor to the transducer module,
    wherein the controller controls the motor to rotate at a preset speed.

6. The ultrasound imaging apparatus of claim 1, wherein the controller controls the ultrasound probe to determine the backlash value when the ultrasound probe is connected to a main body of the ultrasound imaging apparatus.

7. The ultrasound imaging apparatus of claim 1, further comprising an inputter configured to receive an input from a user,
    wherein the controller controls the ultrasound probe to determine the backlash value in response to receiving the input about photographing a three dimensional (3D) ultrasound image through rotation of the transducer module from the user, or receiving the input about determining the backlash value.

8. The ultrasound imaging apparatus of claim 1, wherein the controller controls the ultrasound probe at preset time intervals to determine the backlash value.

9. The ultrasound imaging apparatus of claim 1, further comprising:
    a display configured to display an ultrasound image,
    wherein the controller controls the display to output a notification or controls the ultrasound probe to determine the backlash value again when the backlash value exceeds a preset threshold value.

10. The ultrasound imaging apparatus of claim 1, wherein the controller, when controlling the driving device to switch the rotating direction of the transducer module, controls the driving device to output a rotary power in one of the first direction and the second direction during a time extended from a preset time by a delayed time corresponding to the backlash value.

11. The ultrasound imaging apparatus of claim 1, wherein the controller shifts a rendering image corresponding to the first direction and a rendering image corresponding to the second direction from a central axis of the transduce module in directions corresponding thereto by an angle, by which each rendering image the first or second direction is shifted for a delayed time corresponding to the backlash value, to generate a result rendering image of the ultrasound image.

12. The ultrasound imaging apparatus of claim 1, wherein the controller determines a time difference between the first switching time point and the second switching time point as a third time, and determines an error time shortened by a delayed time corresponding to the backlash value from the third time due to hysteresis characteristics of the position sensor.

13. The ultrasound imaging apparatus of claim 12, wherein when a first point of time, at which the output signal is switched from the second signal to the first signal as a result of the transducer module rotating in the first direction, is set as a central axis of the transducer module, the controller determines a shifted point of time shifted, in the first direction for the error time, from a second point of time, at which the output signal is switched from the first signal to the second signal as a result of the transducer module rotating in the second direction, as the central axis of the transducer module, so that the shifted point of time matches the first point of time.

14. A method of controlling an ultrasound imaging apparatus comprising an ultrasound probe including a transducer module including an ultrasound transducer array, a driving device configured to rotate the transducer module, a magnet configured to rotate as a result of rotation of the transducer module, and a position sensor configured to output one of a first signal and a second signal on the basis of a change in magnetic flux density according to rotation of the magnet, the method comprising:
 determining a first time for which the first signal is output as the transducer module rotates in a first direction;
 controlling the driving device to switch a rotating direction of the transduce module from the first direction to a second direction at a first switching time point at which an output signal is switched from the first signal to the second signal;
 controlling the driving device to switch the rotating direction of the transducer module during a same time as the first time, starting from a second switching time point at which the output signal is switched from the second signal to the first signal after the first switching time point;
 determining a second time for which the first signal is output after the second switching time point; and
 determining a backlash value on the basis of a difference value between the first time and the second time, wherein the position sensor switches the output signal from the second signal to the first signal when the magnetic flux density reaches a first magnetic flux density as the magnet moves toward the position sensor, and switches the output signal from the first signal to the second signal when the magnetic flux density reaches a second magnetic flux density as the magnet moves away from the position sensor, wherein the first signal and the second signal are different from each other due to the position sensor's hysteresis characteristics, and wherein the determining of the first time comprises:
 determining a third switching time point, which is a time point before the first switching time point, at which the output signal is switched from the second signal to the first signal as the magnet moves toward the position sensor as a result of the transducer module rotating in the first direction; and
 determining a time difference between the third switching time point and the first switching time point.

15. The method of claim 14, wherein the determining of the backlash includes determining the backlash value by dividing the difference value between the first time and the second time by a number of times the rotating direction of the transducer module is switched during the same time as the first time, starting from the second switching time point.

16. The method of claim 14, further comprising controlling the driving device to rotate the transducer module in one of the first direction and the second direction within a preset time from the second switching time point at which the rotating direction of the transducer module is switched, during the same time as the first time, starting from the second switching time point.

17. The method of claim 14, wherein the position sensor switches the output signal from the second signal to the first signal when the magnetic flux density reaches a first magnetic flux density as the magnet moves toward the position sensor, and switches the output signal from the first signal to the second signal when the magnetic flux density reaches a second magnetic flux density as the magnet moves away from the position sensor.

* * * * *